(12) United States Patent
Peterchev

(10) Patent No.: US 9,345,901 B2
(45) Date of Patent: May 24, 2016

(54) SYSTEMS AND METHODS FOR INDUCING ELECTRIC FIELD PULSES IN A BODY ORGAN

(75) Inventor: Angel Vladimirov Peterchev, Durham, NC (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 1008 days.

(21) Appl. No.: 13/321,073

(22) PCT Filed: May 19, 2010

(86) PCT No.: PCT/US2010/035401
§ 371 (c)(1),
(2), (4) Date: Jan. 17, 2012

(87) PCT Pub. No.: WO2010/135425
PCT Pub. Date: Nov. 25, 2010

(65) Prior Publication Data
US 2012/0108883 A1 May 3, 2012

Related U.S. Application Data

(60) Provisional application No. 61/179,590, filed on May 19, 2009, provisional application No. 61/225,644, filed on Jul. 15, 2009.

(51) Int. Cl.
*A61N 1/00* (2006.01)
*A61N 2/02* (2006.01)
*A61N 1/40* (2006.01)

(52) U.S. Cl.
CPC .... *A61N 2/02* (2013.01); *A61N 1/40* (2013.01)

(58) Field of Classification Search
CPC .................................. A61N 2/02; A61N 1/40
USPC .................................. 600/9–14; 128/897–899
See application file for complete search history.

(56) References Cited

U.S. PATENT DOCUMENTS 4,914,540 A  4/1990  Tabata et al.
5,030,196 A  7/1991  Inoue
(Continued)

FOREIGN PATENT DOCUMENTS

EP       1894600 A1    3/2008
WO  WO 2007/145838 A2  12/2007

OTHER PUBLICATIONS

ABB Switzerland Ltd. (2005). HiPak™ GBT Modues with SPT Chips. From http://www.abb.com/semiconductors.
(Continued)

*Primary Examiner* — Navin Natnithithadha
*Assistant Examiner* — Sunita Reddy
(74) *Attorney, Agent, or Firm* — Potomac Law Group PLLC

(57) ABSTRACT

Systems and methods for providing controllable pulse parameter magnetic stimulation are described. One aspect is directed to a magnetic stimulation system for inducing approximately rectangular electric field pulses in a body organ, comprising an electrical energy storage device, a stimulating coil, and a switching means for electrically coupling said electrical energy storage device to said stimulating coil to produce current pulses in said stimulating coil which generates, in response to the current pulses, magnetic field pulses that can induce approximately rectangular electric field pulses in the body organ.

12 Claims, 23 Drawing Sheets

(56) References Cited

U.S. PATENT DOCUMENTS

| | | | |
|---|---|---|---|
| 5,047,005 | A | 9/1991 | Cadwell |
| 5,327,854 | A | 7/1994 | Smith et al. |
| 5,707,334 | A | 1/1998 | Young |
| 5,769,778 | A | 6/1998 | Abrams et al. |
| 5,813,970 | A | 9/1998 | Abrams et al. |
| 5,833,600 | A | 11/1998 | Young |
| 6,117,066 | A | 9/2000 | Abrams et al. |
| 6,123,658 | A | 9/2000 | Schweighofer et al. |
| 6,179,770 | B1 | 1/2001 | Mould |
| 6,198,958 | B1 | 3/2001 | Ives et al. |
| 6,402,678 | B1 | 6/2002 | Fischell et al. |
| 6,551,233 | B2 | 4/2003 | Perreault et al. |
| 6,572,528 | B2 | 6/2003 | Rohan et al. |
| 6,591,138 | B1 | 7/2003 | Fischell et al. |
| 6,899,667 | B2 | 5/2005 | Becker et al. |
| 6,926,660 | B2 | 8/2005 | Miller |
| 6,978,179 | B1 | 12/2005 | Flagg et al. |
| 6,983,184 | B2 | 1/2006 | Price |
| 7,069,067 | B2 | 6/2006 | Kuth |
| 7,087,008 | B2 | 8/2006 | Fox et al. |
| 7,104,947 | B2 | 9/2006 | Riehl |
| 7,130,203 | B2 | 10/2006 | Mbaye |
| 7,153,256 | B2 | 12/2006 | Riehl et al. |
| 7,160,240 | B2 | 1/2007 | Frimerman et al. |
| 7,231,254 | B2 | 6/2007 | DiLorenzo |
| 7,276,020 | B2 | 10/2007 | Becker et al. |
| 7,277,758 | B2 | 10/2007 | DiLorenzo |
| 7,282,021 | B2 | 10/2007 | Rohan et al. |
| 7,294,101 | B2 | 11/2007 | Fischell et al. |
| 7,320,664 | B2 | 1/2008 | Riehl et al. |
| 7,407,478 | B2 | 8/2008 | Zangen et al. |
| 2002/0169355 | A1* | 11/2002 | Rohan et al. ............... 600/9 |
| 2003/0050527 | A1* | 3/2003 | Fox et al. .............. 600/13 |
| 2005/0182288 | A1* | 8/2005 | Zabara ................. 600/14 |
| 2005/0288744 | A1 | 12/2005 | Pilla et al. |
| 2006/0052657 | A9 | 3/2006 | Zabara |
| 2007/0203390 | A1 | 8/2007 | Rohan et al. |
| 2007/0282388 | A1 | 12/2007 | Sandyk |
| 2007/0293916 | A1* | 12/2007 | Peterchev ............. 607/61 |
| 2008/0121232 | A1* | 5/2008 | Cewers ............... 128/204.22 |
| 2008/0200749 | A1* | 8/2008 | Zheng et al. .......... 600/13 |

OTHER PUBLICATIONS

ABB Switzerland Ltd. (2005). IGBT Module 5SNA0900E450100. From http://www.abb.com/semidconductors.

ABB Switzerland Ltd. (2005). Reverse Conducting Integrated Gate-Commutated Thyristor 5SHX26L4510. From http://www.abb.com.

Amassian V. E., Cracco, R. Q., Maccabee, P. J, Cracco, J. B., Rudell, A., and Eberle, L. (1989). Suppression of visual perception by magnetic coil stimulation of human occipital cortex. *Electroencephalogr Clin Neurophysiol*, 74(6), 458-462.

Antal, A., Kincses, T. Z., Nitsche, M. A., Bartfai O, Demmer T., Sommer, M., and Paulus, W. (2002). Pulse configuration-dependent effects of repetitive transcranial magnetic stimulation on visual perception. *Neuroreport*, 13(17), 2229-2233.

Arai, N., Okabe, S., Furubayashi, T., Terao Y., Yuasa, K., and Ugawa, Y. (2005). Comparison between short train, monophasic and biphasic repetitive transcranial magnetic stimulation (rTMS) of the human motor cortex. *Clin Neurophysiol*, 116(3), 605-613.

Barker, A.T., Garnham, C.W., Freeston, T. L. Magnetic nerve stimulation: The effect of waveform on efficiency, determination of neural membrane time constants and the measurement of stimulator output. *Electroencephalogr Clin Neurophysiol*, Suppl., vol. 43, pp. 227-237, 1991.

Barker, A.T., Jalinous, R., Freeston, I.L. Non-Invasive Magnetic Stimulation of Human Motor Cortex. *The Lancet*, May 11, 1985, pp. 1106-1107.

Berardelli, A., Inghilleri, M., Rothwell, J. C., Romeo, S., Curra, A., Gilio, F., Modugno N., and Manfredi, M. (1998). Facilitation of muscle evoked responses after repetitive cortical stimulation in man. *Exp Brain Res*, 122(1), 7984.

Berman, R. M., Sackeim, H. A., Truesdale, M. D,, Luber, B., Schroeder, C., and Lisanby, S. H. (2005). Focal electrically-administered seizure therapy (feast): Nonhuman primate studies of a novel form of focal brain stimulation. *J ECT*, 21 57.

Myers, A. M. Improving the Efficiency of Magnetic Stimulation of Nerves. Department of Medical Physic and Clinical Engineering, The University of Sheffield, Chapter 8, pp. 114-121, Feb. 2005.

Peterchev, Angel V., Jalinous, Reza, and Lisanby, Sarah H. A Transcranial magnetic Stimulator Inducing Near-Rectangular Pulses With Controllable Pulse Width (cTMS). *IEEE* vol. 55, No. 1, Jan. 2008, pp. 257-266.

Peterchev, Angel V., Spellman, Timothy J. and Lisanby, Sarah H. cTMS: A novel TMS Device Inducing Near Rectangular Pulses with Controllable Pulse Width. *Neuropshychopharmacology*, vol. 31, No. 1, ACNP 2006 Annual Meeting, PS130.

Brasil-Neto, J. P., Cohen, L. G., Panizza, M., Nilsson, J., Roth, B. J., and Hallett, M. (1992). Optimal focal transcranial magnetic activation of the human motor cortex: effects of coil orientation, shape of the induced current pulse, and stimulus intensity. *J Clin Neurophysiol*, 9(1), 132-136.

Cadwell, J. (1991). Optimizing magnetic stimulator design. *Electroencephalogr Clin Neurophysiol Suppl.* 43, 238-248.

Chen, R., Classen, J., Gerloff, C., Celnik, P., Wassermann, E. M., Hallet, M., and Cohen, L. G. (1997). Depression of motor cortex excitability by low-frequency transcranial magnetic stimulation. *Neurology*, 48(5), 1398-1403.

Corthout, E., Barker, A. T., and Cowey, A. (2001). Transcranial magnetic stimulation, Which part of the current waveform causes the stimulation? *Exp Brain Res*, 141(1), 128-132.

Curra, A., Modugno, N., Inghilleri, M., Manfredi, M., Hallett, M., and Berardelli, A. (2002). Transcranial magnetic stimulation techniques in clinical investigation. *Neurology*, 59(12), 1851-1859.

Davey, K. and Epstein, C. M. (2000). Magnetic stimulation coil and circuit design. IEEE Trans Biomed Eng, 47(11), 1493-1499.

Di Lazzaro, V., Oliviero, A., Mazzone, P., Pilato, F., Saturno, E., Dileone, M., and Tonali, P. A. (2003). Generation of I waves in the human: spinal recordings. *Suppl Clin Neurophysiol*, 56, 143-152.

Di Lazzaro, V., Oliviero, A., Pilato, F., Saturno, E., Dileone, M., Mazzone, P., Insola, A., Tonali, P. A., and Rothwell, J. C., (2004). The physiological basis of transcranial motor cortex stimulation in conscious humans. *Clin Neurophysiol*, 112), 255-266.

Digitimer Limited. (2005). MultiPulse Stimulator D185—Mk.II. From http://www.digitimer.com.

Dubach, M. F., Tongen, V. C., and Bowden, D. M. (1985). Techniques for improving stereotaxic accuracy in Macaca fascicularis. J Neurosci Methods, 13(2), 163-169.

Epstein, C. M., Schwartzberg, D. G., Davey, K. R., and Sudderth, D. B. (1990). Localizing the site of magnetic brain stimulation in humans. Neurology, 40(4), 666-670.

Esser, S. K., Hill, S. L., and Tononi, G. (2005). Modeling the effects of transcranial magnetic stimulation on cortical circuits. J Neurophysiol, 94(1), 622-639.

European Search Report dated May 29, 2009, European Application No. 07 809261.6.

European Search Report dated Oct. 16, 2009, European Application No. 07 809 261.6.

Fitzgerald, P. B., Benitez, J., de Castella, A., Daskalakis, Z. J., Brown, T. L., and Kulkarni, J. (2006). A randomized, controlled trial of sequential bilateral repetitive transcranial magnetic stimulation for treatment-resistant depression. Am J Psychiatry, 163(1), 38-94.

General Atomics Electronic Systems Inc. (1999). Capacitor Specification. Model No. 310DM475. From http://www.gaep.com/capacitors.html.

General Atomics Electronic Systems Inc. (2003). Series DP: Drawn Metal Can High Voltage Capacitors. From http://www.gaep.com/series-dp-capacitors.html.

Gershon, A. A., Dannon, P. N., and Grunhaus, L. (2003). Transcranial magnetic stimulation in the treatment of depression. *Am J Psychiatry*, 160(5), 835-845.

Huang, Y, Z., Edwards, M. J., Rounis, E., Bhatia, K. P., and Rothwell, J. C, (2005). Theta burst stimulation of the human motor cortex. *Neuron*, 42), 201-206.

International Search Report, dated Sep. 9, 2008, for International Patent Application No. PCT/US07/12825.

Jalinous, R. Technical and practical aspects of magnetic nerve stimulation. J Clin Neurophysiol, vol. 8, No. 1, pp. 10-25, 1991.

Jalinous, R. Principles of magnetic stimulator design. Handbook of Transcranial Magnetic Stimulation, A. Pascual-Leone, N.J. Davey, J. Rothwell, E. M. Wassermann, and B. Arnold, 2002, pp. 30-38.

(56) References Cited

OTHER PUBLICATIONS

Kammer, T., Beck, S., Thielscher, A., Laubis-Herrmann, U., and Topka, H. (2001). Motor thresholds in humans: a transcranial magnetic stimulation study comparing different pulse waveforms, current directions and stimulator types. Clin Neurophysiol, 112(2), 250-258.

Kolachana, B. S., Saunders, R. C., and Weinberger, D. R. (1995). Augmentation of prefrontal cortical monoaminergic activity inhibits dopamine release in the caudate nucleus: an in vivo neurochemical assessment in the rhesus monkey. Neuroscience, 69(3), 859-868.

Komssi, Soile. Electroencephalographic Responses to Transcranial Magnetic Stimulation. University of Helsinki, Report series in Physics, Academic Dissertation, Nov. 27, 2004, pp. 1-47.

Lisanby, S. H, Guthman, D., Luber, B., Schroeder, C., and Sackeim, H. A. (2001). Sham TMS: intracerebral measurement of the induced electrical field and the induction of motor-evoked potentials. *Biol Psychiatry*, 49(5), 460-463.

Lisanby, S. H., Wassermann, E. M., Ziemann, U., Luber, B., Finck, D., Osman, M., Dichter, G., and Sackeim, H. A. (1997). Motor evoked potentials to paired transcranial magnetic stimulation (TMS) in the alert and sedated rhesus monkey. *Electroencephalogr Clin Neurophysiol*, 103, 151.

Martin, R. F. and Bowden, D. M. (1996). A stereotaxic template atlas of the macaque brain for digital imaging and quantitative neuroanatomy. Neuroimage, 4(2), 119-150.

McCreery, D. B., Agnew, W. F., Yuen, T. G., and Bullara, L. (1990). Charge density and charge per phase as cofactors in neural injury induced by electrical stimulation. IEEE Trans Biomed Eng, 37(10), 996-1001.

Merton, P. A. and Morton, H. B. (1980). Stimulation of the cerebral cortex in the intact human subject. Nature, 285(5762), 227.

Nahm, F. K., Dale, A. M., Albright, T. D., and Amaral, D. G. (1994). In vivo microelectrode localization in the brain of the alert monkey: a combined radiographic and magnetic resonance imaging approach. Exp Brain Res, 98(3), 401-411.

Maccabee, P. J., Nagarajan, S. S., Amassian, V. E., Durand, D. M., Szabo, A. Z., Ahad, A. Cracco, B., R. Q., Lai, K. S. and Eberle, L. P. Influence of pulse sequence, polarity and amplitude on magnetic stimulation of human and porcine peripheral nerve. Journal of Physiology (1998), 513.2, pp. 571-585, Received 12, Dec. 1997; Accepted after revision 13, Aug. 1998.

Morales, O.G., Sackeim, H. A., Berman, R. M., and Lisanby, S. H. Magnetic seizure therapy: development of a novel intervention for treatment resistant depression. Clin Neurosci Res, vol. 4, pp. 59-70, 2004.

National Instruments Corp. (2005). NI PCI-7041/6040E. From http://www.ni.com.

National Instruments Corp. (2005). R Series Intelligent DAQ with Onboard Processing. From http://www.ni.com.

Panizza, M., Nilsson, J., Roth, B. J., Basscr, P. J., and Hallett, M. (1992). Relevance of stimulus duration for activation of motor and sensory fibers: implications for the study of H-reflexes and magnetic stimulation. *Electroencephalogr Clin Neurophysiol*, 85(1), 22-29.

Pascual-Leone, A., Tormos, J. M., Keenan, J., Tarazona, F., Canete, C., and Catala, M. D. (1998). Study and modulation of human cortical excitability with transcranial magnetic stimulation. *J Clin Neurophysiol*, 15(4), 333-343.

Pudenz, R. H., Bullara, L. A., Jacques, S., and Hambrecht, F. T. (1975). Electrical stimulation of the brain. III. The neural damage model. *Surg Neurol*, 4(4), 389-400.

Orth, M. and Rothwell, J. C. (2004). The cortical silent period: intrinsic variability and relation to the waveform of the transcranial magnetic stimulation pulse. Clin Neurophysiol, 115(5), 1076-1082.

Roth, B. J. and Basser, P. J. (1990). A model of the stimulation of a nerve fiber by electromagnetic induction. IEEE Trans Biomed Eng, 37(6), 588-597.

Roth, B. J., Cohen, L. G., and Hallett, M. (1991). The electric field induced during magnetic stimulation. Electroencephalogr Clin Neurophysiol Suppl, 43, 268-278.

Ruohonen, Jarmo and Ilmoniemi, Risto J. Basic Physics and Design of Transcranial Magnetic Stimulation Devices and Coils. Magnetic Stimulation in Clinical Neurophysiology, M. Hallett and S. Chokroverty, Eds., 2nd ed., Philadelphia, PA: Elsevier Butterworth-Heinemann, 2005, pp. 17-30.

Sackeim, H. A., Long, J., Luber, B., Moeller, J. R., Prohovnik, I., Devanand, D. P., and Nobler, M. S. (1994). Physical properties and quantification of the ECT stimulus: I. Basic principles. Convuls Ther, 10(2), 93-123.

Saunders, R. C., Aigner, T. G., and Frank, J. A. (1990). Magnetic resonance imaging of the rhesus monkey brain: use for stereotactic neurosurgery. *Exp Brain Res*, 81(2), 443-446.

Saunders, R. C., Kolachana, B. S., and Weinberger, D. R. (1994). Local pharmacological manipulation of extracellular dopamine levels in the dorsolateral prefrontal cortex and caudate nucleus in the rhesus monkey: an in vivo microdialysis study. Exp Brain Res, 98(1), 44-52.

Schroeder, C. E., Mehta, A. D., and Givre, S. J. (1998). A spatiotemporal profile of visual system activation revealed by current source density analysis in the awake macaque. Cereb Cortex, 8(7), 575-592.

Schroeder, C. E., Steinschneider, M., Javitt, D. C., Tenke, C. E., Givre, S. J., Mehta, A. D., Simpson, G. V., Arezzo, J. C., and Vaughan, H. G., Jr. (1995). Localization of ERP generators and identification of underlying neural processes. Electroencephalogr Clin Neurophysiol Suppl, 44, 55-75.

Sommer, M., Lang, N., Tergau, F., and Paulus, W. (2002). Neuronal tissue polarization induced by repetitive transcranial magnetic stimulation? Neuroreport, 13(6), 809-811.

Szabo, J. and Cowan, W. M. (1984). A stereotaxic atlas of the brain of the cynomolgus monkey (*Macaca fascicularis*). J Comp Neurol, 222(2), 265-300.

Taylor, J. L. and Loo, C K. Stimulus waveform influences the efficacy of repetitive transcranial magnetic stimulation. J Affect Disord, vol. 97, pp. 271-276, 2007.

Tings, T., Lang, N., Tergau, F., Paulus, W., and Sommer, M. (2005). Orientation-specific fast rTMS maximizes corticospinal inhibition and facilitation. *Exp Brain Res*, 164(3), 323-333.

Tofts, P. S. and Branston, N. M. (1991). The measurement of electric field, and the influence of surface charge, in magnetic stimulation. *Electroencephalogr Clin, Neurophysiol*, 81(3), 238-239.

W. Paulus et al. Transcranial Magnetic Stimulation, Proceedings of the International Symposium on Transcranial Magnetic Stimulation. Gottingen, Germany, Sep. 30 to Oct. 4, 1998, *Electroencephalography and Clinical Neurophysiology*, Suppl. 51., pp. 7-10, 1999.

Walsh, V. and Cowey, A. (2000). Transcranial magnetic stimulation and cognitive neuroscience. *Nat Rev Neurosci*, 1(1), 73-79.

Wassermann, E. M. and Lisanby, S. H. (2001). Therapeutic application of repetitive transcranial magnetic stimulation: a review. *Clinical Neurophysiol*. 112(8), 1 3671 377.

Weiner, R D. (1980). ECT and seizure threshold: effects of stimulus wave from and electrode placement. *Biol Psychiatry*, 15(2), 225241.

Weiner, R. D. and Coffey, C. E. (1989). Comparison of Brief Pulse and Sine Wave ECT Stimuli. *Convuls Ther*, 5(2), 184185.

Weissman, J. D., Epstein, C. M., and Davey, K. R. (1992). Magnetic brain stimulation and brain size: relevance to animal studies. *Electroencephalogr Clin Neurophysiol*, 85(3), 21 521 9.

Written Opinion of the International Searching Authority dated Sep. 9, 2008.

Extended European Search Report and Search Opinion issued Mar. 13, 2012, in European Patent Application No. 10778324.3.

Jovanovic et al., "Evaluation of Active and Passive Snubber Techniques for Applications in Power-Factor-Correction Boost Converters", Sixth International Conference on Power Semiconductors and their Applications (Electronica '92), Munchen, Germany, Nov. 11, 1992, pp. 105-115, XP055186144.

Extended European Search Report issued May 11, 2015, in European Patent Application No. EP 14192737.6.

* cited by examiner

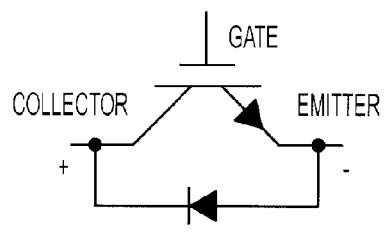
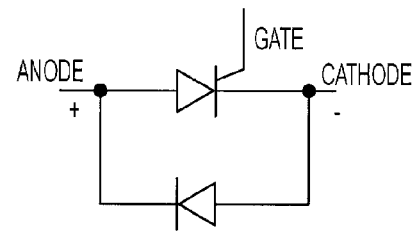
FIG. 3B                    FIG. 3C

| PARAMETER | SYMBOL | MONOPHASIC MAGNETIC PULSE | | | BIPHASIC MAGNETIC PULSE | | | | | UNIT |
|---|---|---|---|---|---|---|---|---|---|---|
| | | MAGSTIM 200 | MAGPRO X100 | cTMS1 | MAGSTIM RAPID2 | NEURONETICS 2100 | cTMS2 | cTMS3 | cTMS4 | |
| POSITIVE CAPACITOR VOLTAGE | $V_{C1}$ | 1,316 | 1,506 | 1,506 | 1,076 | 1,645 | 1,645 | 1,645 | 2,800 | V |
| NEGATIVE CAPACITOR VOLTAGE | $-V_{C2}$ | - | - | -602 | - | - | -165 | -411 | -700 | V |
| COIL CURRENT RISE TIME | $t_{RISE}$ | 86 | 70 | 42 | 173* | 100* | 42* | 49* | 31* | μs |
| COIL DISCHARGE TIME CONSTANT | $T_{FALL} = L/R$ | 182 | 204 | - | - | - | - | - | - | μs |
| EFFECTIVE PW ** | $PW_{eff}$ | 70 | 60 | 42 | 92 | 54 | 35 | 35 | 20 | μs |
| PEAK COIL ENERGY | $W_L = 1/2 L I_{Lpk}^2$ | 136 | 123 | 97 | 89 | 74 | 58 | 60 | 52 | J |
| ENERGY DISSIPATION/PULSE W/ IRON CORE | $\Delta W_C$ | 160 | 142 | 21/48*** | 48 | 25 | 26 | 21 | 27 | J |
| W/O IRON CORE | $\Delta W_C$ | 40 | 36 | 5/12** | 12 | 6 | 7 | 5 | 7 | J |
| LOAD INTEGRAL | $\int i_L^3 dt$ | 2,483 | 2,217 | 503 | 1,693 | 859 | 797 | 517 | 352 | A²s |
| W/ IRON CORE | $\int i_L^2 dt$ | 621 | 554 | 126 | 423 | 215 | 199 | 129 | 88 | A²s |
| MAX. MEMBRANE DEPOLARIZATION | $MAX(\Delta V_m)$ | 18 | 18 | 18 | 18 | 18 | 18 | 18 | 18 | mV |
| HYPERPOLARIZATION/ DEPOLARIZATION RATIO | $-MIN(\Delta V_m) / MAX(\Delta V_m)$ | 0.25 | 0.22 | 0.37 | 0.81 | 0.83 | 0.27 | 0.50 | 0.65 | - |

(*) FOR BIPHASIC PULSES, RISE TIME EQUALS INTERVAL BETWEEN PEAK NEGATIVE AND PEAK POSITIVE CURRENT
(**) EFFECTIVE PW = TIME INTERVAL FROM ZERO TO PEAK NEURONAL MEMBRANE DEPOLARIZATION
(***) (ASSUMING IDEAL CONVERSION OF ENERGY FROM C2 TO C1 AFTER PULSE)/(ASSUMING 70% CONVERSION EFFICIENCY)

FIG. 11

SYSTEMS AND METHODS FOR INDUCING ELECTRIC FIELD PULSES IN A BODY ORGAN

CROSS-REFERENCE TO RELATED APPLICATIONS

This application is a U.S. national stage application of International Application No. PCT/US2010/035401, filed on May 19, 2010, which claims priority to, and the benefit of, U.S. Provisional Application No. 61/255,644, filed on Jul. 15, 2009, and U.S. Provisional Application No. 61/179,590, filed on May 19, 2009, the entirety of all of which applications are hereby incorporated herein by reference.

FIELD

The disclosed subject matter relates to systems and methods for providing controllable pulse parameter magnetic stimulation that induces electric field pulses in a body organ.

BACKGROUND

Magnetic stimulation is a noninvasive tool for the study of the human brain and peripheral nerves that is being investigated as a potential therapeutic agent in psychiatry and neurology. When applied to the brain, this technique is commonly referred to as Transcranial Magnetic Stimulation (TMS). However, the term "TMS" is often used to refer to magnetic stimulation of other body organs as well. Therefore, the term TMS will be used hereinafter to refer to magnetic stimulation of the brain or other body organs.

In TMS, a pulsed current sent through a coil produces a magnetic field that induces an electric field in the brain, which can affect neuronal activity. A single TMS pulse can activate a targeted brain circuit. For example, a TMS pulse delivered to the motor cortex can result in a twitch of the associated muscles in the body. Further, a single TMS pulse can also disrupt neural activity. For example, a TMS pulse delivered to the occipital cortex can mask the perception of a visual stimulus. This allows researchers to probe brain circuits on a millisecond time scale.

A train of TMS pulses, referred to as repetitive TMS (rTMS), can produce excitatory or inhibitory effects which last beyond the stimulation interval. Repetitive TMS provides a means to study higher cognitive functions, and it could potentially be used as a therapeutic intervention in psychiatry and neurology.

The neural response to TMS is sensitive to the parameters of the stimulating TMS pulse. The pulse width (PW), shape (e.g., sinusoidal vs. rectangular), and the relative amplitude of the positive and negative phases (degree of bidirectionality) of the induced electric field affect the physiological response to TMS, the power efficiency of the stimulator, and the heating of the stimulating coil. Existing TMS systems are capable of inducing only damped cosine electric field pulse shapes, with a limited set of discrete choices of pulse width and degree of bidirectionality. Further, in existing TMS systems, monophasic magnetic field pulse shapes are associated with very low power efficiency of the stimulator in rTMS applications.

DESCRIPTION

Systems and methods are disclosed for providing controllable pulse parameter magnetic stimulation that induces electric field pulses in a body organ. One aspect is directed to a magnetic stimulation system for inducing approximately rectangular electric field pulses in a body organ, comprising an electrical energy storage device, a stimulating coil, and a switching means for electrically coupling said electrical energy storage device to said stimulating coil to produce current pulses in said stimulating coil which generates, in response to the current pulses, magnetic field pulses that can induce approximately rectangular electric field pulses in the body organ.

Another aspect is directed to a magnetic stimulation system for inducing approximately rectangular electric field pulses in a body organ, comprising a first and a second electrical energy storage device, a stimulating coil, a first switching means to electrically couple said first electrical energy storage device to the stimulating coil to produce current pulses with a positive rate of change in the stimulating coil, and a second switching means to electrically couple said second electrical energy storage device to said stimulating coil to produce current pulses with a negative rate of change in the stimulating coil, wherein the stimulating coil produces, in response to a combination of the current pulses with the positive and negative rates of change, magnetic field pulses that can induce approximately rectangular electric field pulses in the body organ.

Another aspect is directed to a method of inducing approximately rectangular electric field pulses in a body organ with a magnetic stimulation system. The method comprises providing a first and a second energy storage device, providing a stimulating coil, providing a first switching means electrically coupled to the first energy storage device and the stimulating coil, providing a second switching means electrically coupled to the second energy storage device and the stimulating coil, actuating the first switching means to electrically couple the first energy storage device to the stimulating coil for a first period of time to produce current pulses with a positive rate of change in the stimulating coil, actuating the second switching means to electrically couple the second energy storage device to the stimulating coil for a second period of time to produce current pulses with a negative rate of change in the stimulating coil, and thereby causing the stimulating coil to produce, in response to a combination of the current pulses with the positive and negative rates of change, magnetic field pulses that can induce approximately rectangular electric field pulses in the body organ, and positioning the stimulating coil proximate to the body organ and exposing the body organ to the magnetic field pulses thereby inducing the approximately rectangular electric field pulses in the body organ.

Another aspect is directed to a magnetic stimulation system for inducing adjustable pulse width electric field pulses in a body organ, comprising an electrical energy storage device, a stimulating coil; and a switching means for electrically coupling said electrical energy storage device to said stimulating coil to produce selectively-adjustable-width current pulses in said stimulating coil which generates, in response to the current pulses, magnetic field pulses that can induce selectively-adjustable-width electric field pulses in the body organ.

Another aspect is directed to a method of inducing adjustable pulse width electric field pulses in a body organ. The method comprises providing an electrical energy storage device, providing a switching means, providing a stimulating coil, and electrically coupling said electrical energy storage device to said stimulating coil with said switching means to produce selectively-adjustable-width current pulses in said stimulating coil which generates, in response to the current pulses, magnetic field pulses that can induce selectively-adjustable-width electric field pulses in the body organ.

Another aspect is directed to a magnetic stimulation system for inducing electric field pulses with an adjustable degree of bidirectionality in a body organ, comprising a first and a second electrical energy storage device, a charging means electrically coupled to the first and second electrical energy storage devices for charging the first electrical energy storage device to a selectable first voltage and charging the second electrical energy storage device to a selectable second voltage, a stimulating coil, a first switching means to electrically couple the first electrical energy storage device to the stimulating coil to produce current pulses with a positive rate of change in the stimulating coil, and a second switching means to electrically couple the second electrical energy storage device to said stimulating coil to produce current pulses with a negative rate of change in the stimulating coil, wherein the stimulating coil produces, in response to a combination of the current pulses with the positive and negative rates of change, magnetic field pulses that can induce electric field pulses in the body organ, the degree of bidirectionality being determined by the ratio of the selectable first voltage and the selectable second voltage.

Another aspect is directed to a method of inducing electric field pulses with an adjustable degree of bidirectionality in a body organ. The method comprises providing a first and a second electrical energy storage device, providing a charging means electrically coupled to the first and second electrical energy storage devices for charging the first electrical energy storage device to a selectable first voltage and charging the second electrical energy storage device to a selectable second voltage, providing a stimulating coil, providing a first switching means electrically coupled to the first electrical energy storage device and the stimulating coil, providing a second switching means electrically coupled to the second electrical energy storage device and the stimulating coil, setting a desired degree of bidirectionality by selecting respective amplitudes for the first and second voltages, the degree of bidirectionality being determined by the ratio of the selected first voltage and the selected second voltage, actuating said first switching means to electrically couple the first electrical energy storage device to the stimulating coil for a first period of time to produce current pulses with a positive rate of change in the stimulating coil, actuating said second switching means to electrically couple the second electrical energy storage device to the stimulating coil for a second period of time to produce current pulses with a negative rate of change in the stimulating coil, and thereby causing the stimulating coil to produce magnetic field pulses in response to a combination of the current pulses with the positive and negative rates of change; and positioning the stimulating coil proximate to the body organ and exposing the body organ to the magnetic field pulses thereby inducing electric field pulses in the body organ with the desired degree of bidirectionality.

Another aspect is directed to a magnetic stimulation system for inducing electric field pulses in a body organ, comprising an electrical energy storage device, a stimulating coil, a switching means for electrically coupling said electrical energy storage device to said stimulating coil to produce current pulses in said stimulating coil which generates, in response to the current pulses, magnetic field pulses that can induce electric field pulses in the body organ, the electric field pulses having a plurality of selectively adjustable parameters from a group consisting of amplitude, pulse width, degree of bidirectionality and pulse repetition frequency; and an operator-controlled apparatus including means for independently controlling at least two of said parameters.

Another aspect is directed to a method for inducing electric field pulses in a body organ with a magnetic stimulation system. The method comprises providing an electrical energy storage device, providing a stimulating coil, electrically coupling said electrical energy storage device to said stimulating coil with a switching means to produce current pulses in said stimulating coil which generates, in response to the current pulses, magnetic field pulses that can induce electric field pulses in the body organ, the electric field pulses having a plurality of selectively adjustable parameters from a group consisting of amplitude, pulse width, degree of bidirectionality and pulse repetition frequency, detecting physiological effects induced in the body organ by the electric field pulses, and controlling at least two of said parameters based on the detected physiological effects.

Another aspect is directed to a magnetic stimulation system for inducing approximately rectangular electric field pulses in a body organ, comprising an electrical energy storage device, a stimulating coil, and a switching circuit configured for electrically coupling said electrical energy storage device to said stimulating coil to produce current pulses in said stimulating coil which generates, in response to the current pulses, magnetic field pulses that can induce approximately rectangular electric field pulses in the body organ.

Another aspect is directed to a method for inducing approximately rectangular electric field pulses in a body organ, comprising storing electrical energy M in an electrical energy storage device, generating with a stimulating coil magnetic field pulses that can induce electric field pulses in the body organ, and switchably electrically coupling the electrical energy storage device to the stimulating coil to produce current pulses in the stimulating coil which generates, in response to the current pulses, magnetic field pulses that can induce approximately rectangular electric field pulses in the body organ.

In a first embodiment, two energy storage capacitors are connected to a common ground. A positive pulse is created in a transcranial magnetic stimulation (TMS) coil by connecting it between a first of two capacitors and ground for a first interval of time and then disconnecting the first capacitor and permitting a current to continue to flow through the TMS coil through a first diode connected between the coil and ground and a second diode connected between the coil and a second capacitor, thereby charging the second capacitor using the magnetic field energy stored in the TMS coil.

In a second embodiment, two energy storage capacitors are connected to a common ground. A positive pulse is created in a transcranial magnetic stimulation (TMS) coil by connecting it between a first of two capacitors and a second of the two capacitors for a first interval of time and then disconnecting the first capacitor and permitting a current to continue to flow through the TMS coil through a first diode connected between the coil and ground and a second diode connected between the coil and the second capacitor, thereby charging the second capacitor using the magnetic field energy stored in the TMS coil. In this embodiment, the first capacitor voltage may be higher than the second.

In either of the above two embodiments, the coil can be short-circuited by closing respective switches on either side of the TMS coil to connect either side of the TMS coil together. In a variation this causes both sides of the TMS coil to be connected to ground.

In either of the embodiments, a negative voltage is applied across the TMS coil by closing third and fourth switches.

Another aspect is directed to a magnetic stimulation system for inducing approximately rectangular electric field pulses in a body organ, comprising a first and second electrical energy storage device, a stimulating coil, a first and second switching means to electrically couple said first electrical energy storage device to the stimulating coil to produce current pulses with a positive rate of change in the stimulating coil, and a third and fourth switching means to electrically couple said second electrical storage device to said stimulating coil to produce current pulses with a positive rate of change in the stimulating coil, wherein the stimulating coil produces, in response to a combination of the current pulses with the positive rates of change, magnetic field pulses that can induce approximately rectangular electric field pulses in the body organ.

Another aspect is directed to a method of inducing approximately rectangular electric field pulses in a body organ with a magnetic stimulation system. The method comprises providing a first and second energy storage device, providing a stimulating coil, providing a first and second switching means coupled to the first energy storage device and the stimulating coil, providing a third and fourth switching means electrically coupled to the second energy storage device and the stimulating coil, actuating the first and second switching means to electrically couple the first energy storage device to the stimulating coil for a first period of time to produce current pulses with a positive rate of change in the stimulating coil, actuating the third and fourth switching means to electrically couple the second energy storage device to the stimulating coil for a second period of time to produce current pulses with a negative rate of change in the stimulating coil, and thereby causing the stimulating coil to produce, in response to a combination of the current pulses with the positive rates of change, magnetic field pulses that can induce approximately rectangular electric field pulses in the body organ, and positioning the stimulating coil proximate to the body organ and exposing the body organ to the magnetic field pulses thereby inducing the approximately rectangular electric field pulses in the body organ.

In a variation of the above, the two energy storage devices include two capacitors, each charged to a different voltage level relative to a common ground. The circuit common ground can be directly connected to earth ground. For a positive phase of a pulse sequence, a first capacitor with a voltage V1 is applied to the coil with a polarity relative to ground to generate a forward current. Then the first capacitor is disconnected allowing current in the coil to decline over an interval. Then a voltage from the second capacitor is applied to the coil to generate a negative current opposite to the direction of the forward current for another interval after which the voltage from the second capacitor is disconnected causing the current to decline for another interval.

BRIEF DESCRIPTION OF THE DRAWINGS

FIG. 3B is an illustrative schematic diagram of an insulated-gate bipolar transistor switch with an anti-parallel diode.

FIG. 3C is an illustrative schematic diagram of a gate turn-off thyristor with an anti-parallel diode.

FIG. 11 is a table of pulse performance metrics used to evaluate the efficiency of controllable pulse parameter transcranial magnetic stimulation pulses.

DETAILED DESCRIPTION

The disclosed subject matter provides, among other things, a controllable pulse parameter transcranial magnetic stimulation (cTMS) system that induces approximately rectangular electric field pulses in an organ of a body, such as a human brain for example. The amplitude, pulse width, and degree of bidirectionality of the induced electric field pulses are adjustable over a continuous range of values. The degree of bidirectionality is defined as the ratio of the positive phase amplitude to the negative phase amplitude of the induced electric field pulse. By adjusting the degree of bidirectionality, the induced electric field pulse can be varied from bipolar (i.e., equal amplitudes of the positive and negative phases) to predominantly unipolar (i.e., a large amplitude of one phase for one polarity and a small amplitude of the other phase for the opposite polarity).

In some embodiments, the cTMS system disclosed herein switches a stimulating coil between positive-voltage and negative-voltage energy storage capacitors or capacitor banks using high-power semiconductor devices. Controlling the pulse parameters facilitates enhancement of TMS as a probe of brain function and as a potential therapeutic intervention. Independent control over the pulse parameters (e.g., pulse width, pulse amplitude, degree of bidirectionality, pulse repetition frequency) facilitates defining dose-response relationships for neuronal populations and producing clinical and physiological effects. For example, dose-response relationships for specific neuronal populations can be defined, and selected clinical and physiological effects can be enhanced. Moreover, the cTMS system disclosed herein also enables high-frequency (>1 Hz) repetitive TMS (rTMS) with predominantly unipolar induced electric fields.

Figure 1:
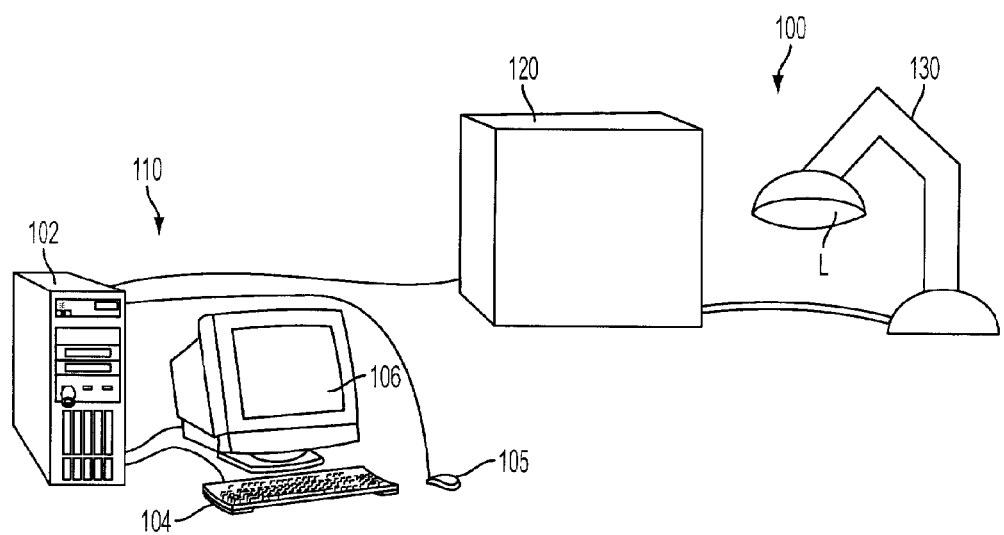
FIG. 1 is an illustrative component diagram of a controllable pulse parameter transcranial magnetic stimulation system, according to some embodiments of the disclosed subject matter.

Referring to FIG. 1, in one embodiment, an illustrative component diagram of a controllable pulse parameter transcranial magnetic stimulation system 100 is shown. The cTMS system 100 includes a power electronics housing 120, a positioning arm 130, a stimulating coil L, and a digital data processing device, such as control computer electronics 110. The control computer electronics 110 includes a control computer electronics housing 102 with analog-digital interface devices, a digital data processing device, and a storage device (e.g., a hard disk), a keyboard 104, a monitor 106, and a mouse 105 (or trackball), and/or other data entry devices. The power electronics circuitry in housing 120 includes cTMS system power electronics that supply current to the stimulating coil L, which can be positioned and held proximate to a patient's head by the positioning arm 130. The power electronics circuitry in the power electronics housing 120 is controlled by the control computer electronics 110. An operator, operating the control computer electronics 110, controls the power electronics in power electronics housing 120 to produce one or more adjustable current pulses that are passed through the stimulating coil L held by positioning arm 130. During a medical treatment, the stimulating coil L is positioned proximate to a patient's head. The adjustable current pulses that are passed through the stimulating coil L result in the stimulating coil L generating adjustable magnetic field pulses, which induce adjustable electric field pulses which, in turn, induce adjustable current pulses in the patient's brain.

Figure 2A:
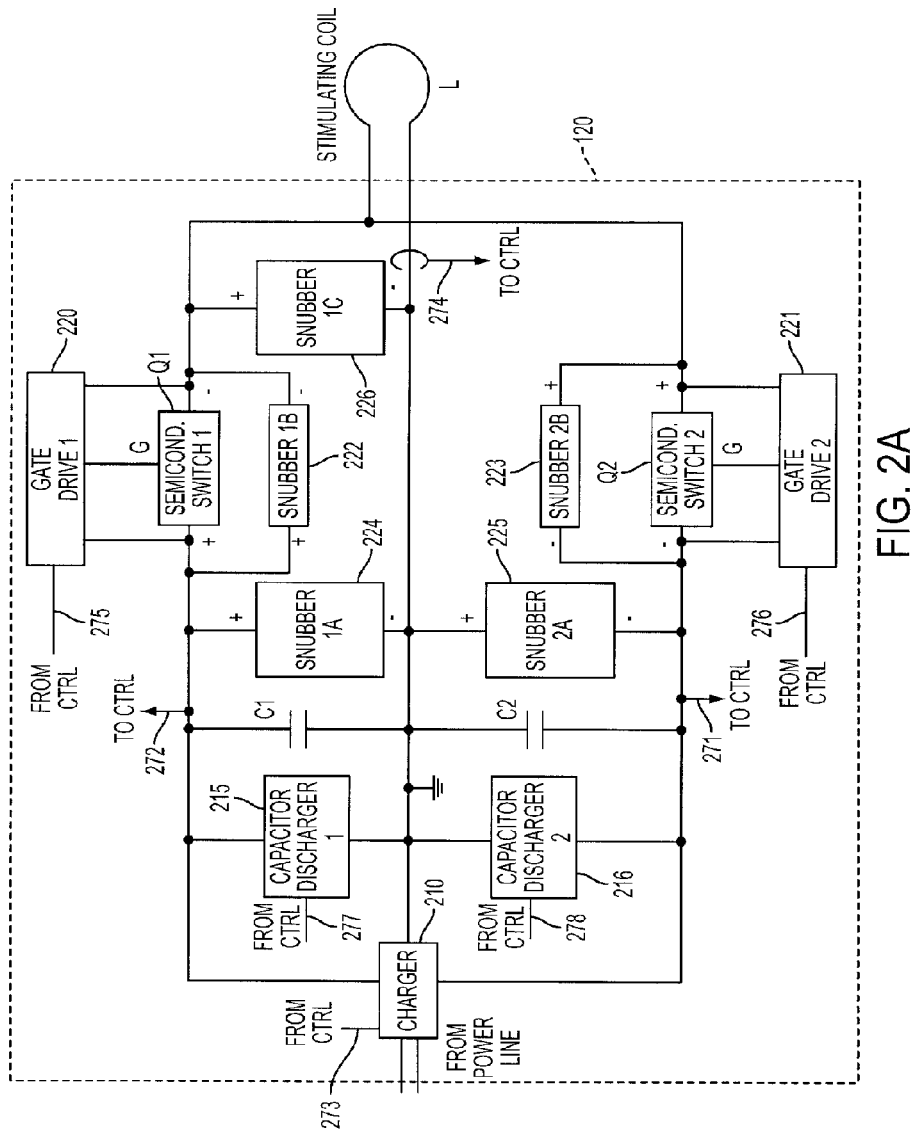
FIG. 2A is an illustrative block diagram of an embodiment of the power electronics circuitry for the controllable pulse parameter transcranial magnetic stimulation system of FIG. 1.
Figure 2B:
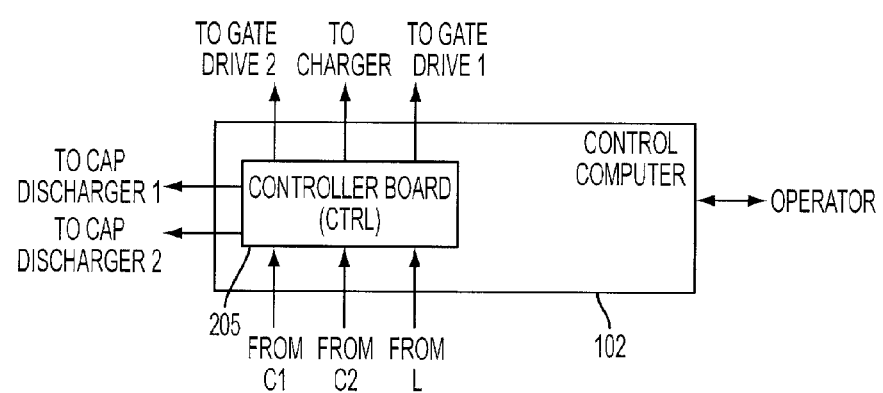
FIG. 2B is an illustrative block diagram of an embodiment of the control computer electronics for the controllable pulse parameter transcranial magnetic stimulation system of FIG. 1.

Referring to FIGS. 2A and 2B, illustrative block diagrams of embodiments of the power electronics circuitry in housing 120 and the control computer electronics in housing 102 are respectively shown. The power electronics housing 120 houses electronics used to drive the stimulating coil L. The electronics in the housing 120 include a charger 210, a first capacitor C1, a second capacitor C2, a first capacitor discharger 215, a second capacitor discharger 216, a first semiconductor switch Q1, a second semiconductor switch Q2, a first snubber circuit 222, a second snubber circuit 223, a third snubber circuit 224, a fourth snubber circuit 225, a fifth snubber circuit 226, a first gate drive 220, and a second gate drive 221.

The control computer housing 102 houses a typical central processing unit (CPU) (not shown), and various standard printed circuit board slots (not shown). Inserted into one of the slots is a controller board 205 that provides control signals used to control the cTMS system 100, and is discussed in further detail below.

In one embodiment, capacitor C1 and capacitor C2 are single capacitors. In another embodiment, capacitor C1 and capacitor C2 each represent a separate bank of capacitors. The capacitors in each separate bank are connected in parallel and/or in series with each other.

Figure 3A:
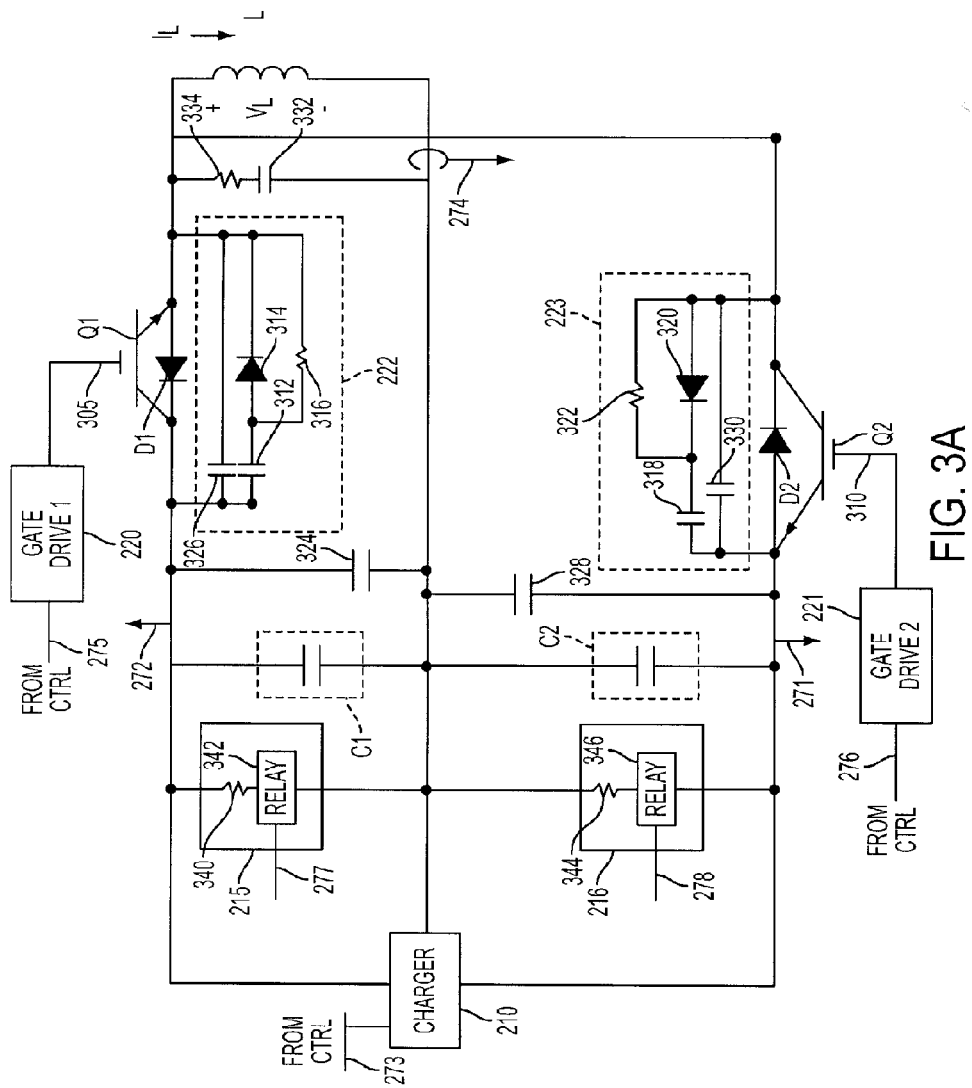
FIG. 3A is an illustrative schematic diagram of another embodiment of the power electronics circuitry for controllable pulse parameter transcranial magnetic stimulation circuit.

Referring to FIG. 3A, an illustrative schematic diagram of the controllable pulse parameter transcranial magnetic stimulation circuit for driving the stimulation coil L is shown. As previously described in connection with the block diagram of FIGS. 2A and 2B, the controllable pulse parameter transcranial magnetic stimulation circuit for driving the stimulation coil L includes energy storage capacitor (or bank of capacitors) C1, energy storage capacitor (or bank of capacitors) C2, controllable semiconductor switch Q1, controllable semiconductor switch Q2, the first and second gate drives 220, 221, and charger 210. The circuit of FIG. 3A additionally includes a diode D1 connected in anti-parallel with the controllable semiconductor switch Q1, and a diode D2 connected in anti-parallel with the controllable semiconductor switch Q2.

Referring again to FIGS. 2A, 2B, and 3A, in one embodiment, an operator controls the cTMS system using the control computer electronics 110. The operator selects cTMS system operation with monophasic or biphasic magnetic pulses and a desired set of induced electric field pulse parameters such as pulse amplitude (A), width of positive pulse phase (PW$^+$), width of initial negative pulse phase (PW$^-$ can be chosen for the biphasic magnetic pulse only), ratio of negative to positive capacitor voltage (M), which determines the degree of bidirectionality, and the frequency of pulse repetition ($f_{train}$) via a graphical user interface (discussed below) executing on the control computer 102. The selected values are stored in the control computer 102.

The controller board 205 is in communication with and controls the charger 210, the first gate drive 220, the second gate drive 221, and capacitor discharger 215 (which includes resistor 340 and normally closed relay 342) and capacitor discharger 216 (which includes resistor 344 and normally closed relay 346) via connections 273, 275, 276, 277, and 278, respectively. The controller board 205 is also in communication with, and receives data from, the energy storage capacitors C1 and C2, and the stimulating coil L via connections 272, 271, 274, respectively.

The charger 210 charges the energy storage capacitor C1 to a positive voltage $V_{C1}$ (set by the operator), and the energy storage capacitor C2 is charged to a negative voltage $-V_{C2}$ (set by the operator). The charger transfers energy from a power line to the capacitors, and transfers energy between the two capacitors. The positive and negative capacitor voltages are independently selectable. Voltage $V_{C1}$ is set based on the pulse amplitude (A) selected by the operator, and voltage $V_{C2}$ is set equal to $M*V_{C1}$, where M is the ratio of negative to positive capacitor voltage selected by the operator. The stimulating coil L is connected to capacitors C1 and C2 via the semiconductor switches Q1 and Q2, and diodes D1 and D2, respectively.

The controller board 205 also supplies separate sets of timing pulses with adjustable widths (set by the operator) to the first and second gate drives 220, 221. The first and second gate drives 220, 221 each use the timing pulses to produce separate sets of voltage pulses with adjustable widths.

In FIG. 3A, each semiconductor switch Q1 and Q2 includes a gate terminal 305 and 310, respectively. The gate terminals 305 and 310 are driven (i.e., clocked) by the voltage pulses supplied by the gate drives 220 and 221. The voltage pulses from controller board 205 are used to switch the semiconductor switches Q1 and Q2 to an on state or an off state. Anti-parallel connected diodes D1 and D2 transfer energy from the stimulating coil L back to capacitors C1 and C2, respectively.

The semiconductor switch Q1 connects coil L to energy storage capacitor C1 for an interval of time equal to the pulse width of the voltage pulses received at the gate terminal 305 from the first gate drive 220, which causes the coil current $I_L$ to increase during this interval of time. When semiconductor switch Q1 is turned off, the coil current commutates to capacitor C2 through diode D2, and the coil current starts to decrease until it reaches zero. Thus, turning switch Q1 on and off results in an approximately triangular positive coil current pulse, which induces an approximately triangular positive monophasic magnetic field pulse. This is discussed in further detail with respect to FIG. 4A. Likewise, the semiconductor switch Q2 connects coil L to energy storage capacitor C2 for an interval of time equal to the pulse width of the voltage pulses received at the gate terminal 310 from the second gate drive 221, which causes the coil current $I_L$ to decrease (i.e., become more negative) during this interval of time. When semiconductor switch Q2 is turned off, the coil current commutates to capacitor C1 through diode D1, and the coil current starts to increase (i.e., become more positive) until it reaches zero. Thus, turning switch Q2 on and off results in an approximately triangular negative coil current pulse, which produces an approximately triangular negative monophasic magnetic field pulse. This is discussed in further detail with respect to FIG. 4B. If an adjustable negative monophasic magnetic field pulse and an adjustable positive monophasic magnetic field pulse are both generated subsequently, an adjustable biphasic magnetic pulse is produced. The approximately triangular magnetic field pulses with adjustable widths induce approximately rectangular electric field pulses in an organ of a body. The approximately rectangular electric field pulses, in turn, induce approximately rectangular, adjustable-pulse-parameter current pulses in an organ of a body, such as a human brain, for example.

The controller board 205 provides timing signals with microsecond resolution to control the semiconductor switches. The cTMS system uses timing of the turn-on and turn-off transitions of the control signals for both semiconductor switches Q1 and Q2 to provide accurate pulse waveform control.

In one embodiment, the controller board 205 is a PCI card from National Instruments (Austin, Tex.) with additional interface electronics that provides sub-microsecond timing signals. Additional interface electronics includes signal conditioning and isolation circuits such as optocouplers, fiber optic links, isolation transformers, attenuators, amplifiers, and filters, as required to connect the controller board 205 to the power electronics in the power electronics housing 120. The PCI card (controller board 205) resides in the control computer housing 102 that provides a GUI for interfacing and configuring the controller board 205. The control computer housing 102 also houses a mass storage device, such as a hard disk (not shown) for storing data. The GUI is implemented in LabVIEW software (available from National Instruments Corp.). The operator inputs various pulse parameters, which are discussed in detail below. The controller board software computes the corresponding capacitor voltages ($V_{C1}$, $V_{C2}$) and switch timing. The controller board 205 then sends the capacitor voltage commands to the charger 210, capacitor dischargers 215, 216, and the switch timing signals to the gate drives 220, 221. The controller board 205 also samples $V_{C1}$, $V_{C2}$, and $I_L$ (via connections 271, 272, 274) to monitor circuit operation, and inhibits or prevents coil currents from exceeding specifications.

Typically, the controllable semiconductor switches Q1 and Q2 should be able to withstand the peak coil current and the peak voltages appearing across their terminals at the peak pulse repetition frequency. The switches Q1 and Q2 should also have turn-on and turn-off times of no more than a few microseconds. The maximum voltage of the semiconductor switches Q1 and Q2 is ideally $V_{C1}+V_{C2}$. However, during current commutation between the two energy storage capacitors C1 and C2, the switch voltage can overshoot this value due to stray inductance and the finite turn-off and turn-on times of the semiconductor switches Q1 and Q2, and diodes D1 and D2. To address this issue, semiconductor devices with fast switching times should be used.

In one embodiment, insulated gate bipolar transistors (IGBTs—shown in FIG. 3B and available from Powerex of Youngwood, Pa.) are used for the switches Q1 and Q2. In another embodiment, gate-turn-off thyristors (GTOs), such as integrated gate-commutated thyristors (IGCTs) (shown in FIG. 3C) are used for switches Q1 and Q2. Both of these devices can sustain pulse currents of thousands of amperes at voltages of a few kilovolts while turning on and off in a few microseconds. Since these devices can turn off while the coil current is not zero, they are used with the snubber circuits 222, 223, 224, 225, 226 (discussed in detail below) which absorb the energy of the commutation transients, thus inhibiting and/or preventing voltage overshoots that exceed the voltage ratings of the semiconductor switches, and energy dissipation in the semiconductor switches, which occurs during switching.

Unlike the silicon-controlled rectifiers (SCRs) used in conventional stimulators, IGBTs can be both turned on and off from the gate terminal. There are existing IGBT modules with peak voltage/surge current ratings of 3300 Volts/12000 Amperes, 4500 Volts/6000 Amperes, 4500 Volts/9000 Amperes, and 6500 Volts/6000 Amperes, and switching times of about one microsecond, which can be used to implement a cTMS system. These IGBT modules have an integrated ultrafast reverse diode between the emitter and the collector (e.g., D1 and D2 in FIG. 3), which clamps the IGBT reverse voltage, and provides a free-wheeling path for the coil current $I_L$.

IGCTs behave like efficient SCRs when turning on and during conduction, and behave like IGBTs when turning off. The turn-on time for an IGCT is approximately 1 µs, but the turn-off time can be as long as 10 µs. IGCTs with integrated reverse diodes (e.g., D1 and D2) and gate drives (e.g., gate drive 220, 221) are available with ratings of 4500 Volts and 17000 Amperes surge current, providing for robustness of the design.

In the cTMS system, the stimulating coil L is forced to commutate between the two energy storage capacitors C1 and C2 when the coil current is at its peak. Managing the forced commutation transient is a challenging aspect of implementing the cTMS system. The finite turn-off and turn-on times of the semiconductor switches Q1 and Q2, and the stray inductance in the capacitor banks C1 and C2, the switches Q1 and Q2, the diodes D1 and D2, and the wiring between them, can result in voltage overshoots that exceed the voltage ratings of the semiconductor switches, and switching power loss and heating in the semiconductor switches. The stray inductances are reduced and/or minimized by installing the semiconductor switches Q1 and Q2, the diodes D1 and D2, and the capacitor banks C1 and C2 as close together as allowed by the physical dimensions of the components, and interconnecting them with wires or bus bars arranged to minimize the area of the current loop. Still, stray inductance cannot be completely eliminated. For example, a typical capacitor bank series inductance of 150 nH with 7 kA current stores magnetic energy sufficient to produce a 27 kV spike on an IGBT switch with 10 nF collector capacitance, which would exceed the voltage rating of a 4500 V IGBT by 22500 V, resulting in potential damage to the IGBT. Therefore, the snubber circuits 222, 223, 224, 225, 226 are used to slow down the transients, ameliorate power dissipation in the semiconductor switches Q1 and Q2, and provide paths for stray inductances to discharge in order to suppress the voltage overshoots.

In one embodiment, as shown in FIG. 3A, the snubber circuits 222, 223 each include a capacitor 312, 318 in series with a diode 314, 320 and resistor 316, 322, which are in parallel with each other. Snubber circuits 222, 223 each also include capacitors 326, 330. This configuration allows the stimulating coil current to flow through the snubber capacitor 312, 318 when the corresponding semiconductor switch Q1, Q2 is turning off, thus inhibiting and/or preventing voltage overshoots. The snubber capacitor 312, 318 should be large enough to hold the peak switch voltage below its rated limit. If the snubber capacitor 312, 318 is too large, switching losses are increased. Snubber circuit 224 includes capacitor 324, snubber circuit 225 includes capacitor 328, and snubber circuit 226 includes capacitor 332 and resistor 334.

Figure 3D:
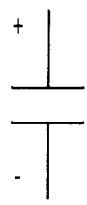
FIGS. 3D-3F are illustrative schematic diagrams of snubber circuits.
Figure 3E:
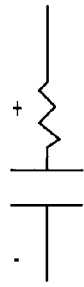
Figure 3F:
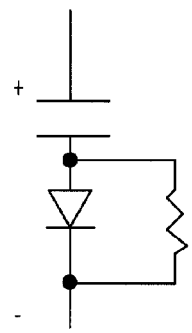

Snubber circuits 222 and 223 (see FIGS. 2A, 3A) can include the circuit embodiments shown in FIGS. 3D, 3E and/or 3F. Snubber circuits 224, 225, and 226 (see FIG. 2A) can include the circuit embodiments shown in FIGS. 3D and/or 3E.

Approaches for sizing of snubber components will be readily understood by those of ordinary skill in the art, and include, but are not limited to, approaches discussed in manufacturer application notes and books on the subject of power electronics.

The gate drives 220, 221 serve to drive (clock) the semiconductor switches Q1 and Q2 to an on state or an off state. As previously discussed, the gate drives 220, 221 receive timing signals from the controller board 205, and apply gate voltages to the gates 305, 310. Some high-power switches, such as IGCTs, are manufactured with an integrated gate drive unit. IGBTs typically require a separate external gate drive. For high-power IGBTs, 10-20 µC is delivered to the gate to raise the gate-emitter voltage to 15-20 Volts to turn on the device. To switch the gate in about 1 µs, IGBT gate drives need an output impedance of a few ohms, and provide peak currents of a few Amperes. IGBT gate drives are available commercially. In some implementations, the gate drives 220, 221 incorporate short-circuit protection which prevents the switch from turning on if a short circuit is detected between the collector and emitter terminals (in IGBTs) or the anode and cathode terminals (in GTOs and IGCTs), which improves the fault tolerance and safety of the cTMS system.

The pulse width control parameters, PW+ and PW" are limited by the discharge of C1 and C2, respectively. To enable pulse width control over a significant range (e.g., up to hundreds of microseconds) and to produce approximately rectangular induced electric field pulses, the energy storage capacitors C1 and C2, in most embodiments disclosed herein, have capacitances in the range of 300 to 800 µF, and 1000 to 3000 µF, respectively. These capacitance values can be accomplished with single pulse capacitors or with banks of parallel and/or series connected pulse capacitors. Suitable capacitor technologies for implementation of C1 and C2 use oil, polypropylene, and/or polyester dielectrics. For example, in one embodiment, C1 is implemented using two parallel 185 µF, 3 kV oil-filled pulse capacitors (e.g., General Atomics model 39504), and C2 is implemented using two parallel 750 µF, 1 kV oil-filled pulse capacitors (e.g., General Atomics model 310DM475). The maximum C1 voltage $V_{C1}$ is 2,800 V, and the minimum (maximum negative) C2 voltage $-V_{C2}$ is 900 V.

Whereas in conventional TMS systems the voltage on the energy storage capacitor is reversed during the pulse, in the disclosed cTMS system the voltages on the capacitors C1 and C2 are never reversed, i.e., always $V_{C1}>0$ and $-V_{C2}<0$. Capacitor voltage reversal decreases the capacitor life expectancy by as much as ten times. Therefore, the energy-storage capacitors C1 and C2 of the disclosed cTMS system have a longer life expectancy since no capacitor voltage reversal occurs.

The capacitor charger 210 for the cTMS system supplies energy to both the capacitors C1 and C2 at two independently controlled DC voltages, $V_{C1}$ and $V_{C2}$, respectively. The capacitor charger 210 also transfers energy from capacitor C2 to capacitor C1 to recover energy accumulated on capacitor C2 after a monophasic positive current pulse in coil L, corresponding to a positive monophasic magnetic field pulse. The capacitor charger 210 also transfers energy from capacitor C1 to capacitor C2 to recover energy accumulated on capacitor C1 after a monophasic negative current pulse in coil L, corresponding to a negative monophasic magnetic field pulse. In one embodiment, a charging unit such as the Magstim Super Charger (available from The Magstim Corp., Whitland, UK) is used to charge the positive capacitor C1. A bidirectional inverting DC/DC power supply is used to transfer energy between capacitor C1 and capacitor C2 so that $V_{C2}$ is maintained at a set level. Capacitor dischargers 215, 216, which constitute a resistor and a normally closed relay connected in series, are included and activated when the energy stored in capacitors C1 and C2 has to be reduced, such as when the pulse amplitude setting A is decreased by the operator, or when the energy stored in capacitors C1 and C2 has to be completely dissipated, such as when the cTMS system is shutdown, power is lost, or a system fault is detected by the controller.

A stimulating coil L known in the art is used with the cTMS system. Both air core and ferromagnetic core coils can be used with the cTMS system. In one embodiment, a coil connector compatible with Magstim 200 coils is used to connect the stimulating coil L to the cTMS circuitry. In one embodiment, a Magstim 16.4 µH 70 mm double stimulating coil (commonly referred to in the art as a figure-of-8) is used.

Due to the rate of change and peak strength of the magnetic field required to achieve transcranial cortical stimulation, TMS systems operate at very high capacitor voltages (up to 3 kV) and peak coil currents (up to 10 kA). In one embodiment, the cTMS system employs maximum positive and negative capacitor voltages of 2800 Volts and –900 Volts, respectively, and a peak coil current of 7 kA.

The currents, voltages, and pulse widths applied to the energy storage capacitors C1 and C2, stimulating coil L, coil cable and connector, and internal wiring in the cTMS system typically do not exceed the currents, voltages, and pulse widths in conventional TMS systems. The cTMS system power consumption in rTMS operation typically does not exceed that of existing TMS systems, since commensurate pulse energies and pulse train frequencies are used. Further, given the higher electrical efficiency of triangular magnetic pulses, the peak values of the pulse parameters could be reduced in comparison with available stimulators. Thus, existing solutions for these system components can be used in the cTMS system.

Figure 4A:
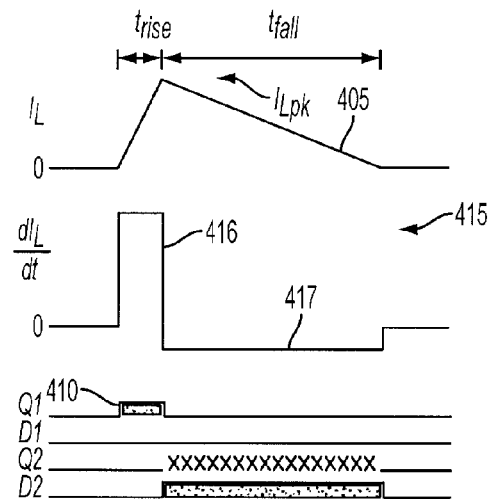
FIG. 4A is an illustrative graph of a positive magnetic pulse generated by using the controllable pulse parameter transcranial magnetic stimulation circuit of FIG. 3A.
Figure 4B:
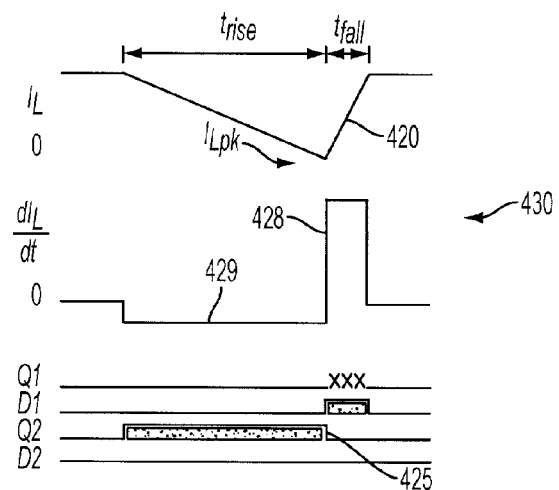
FIG. 4B is an illustrative graph of a negative magnetic pulse generated using the controllable pulse parameter transcranial magnetic stimulation circuit of FIG. 3A.

An analysis of the cTMS circuit shown in FIG. 3A will now be presented in connection with FIGS. 4A, 4B. For this analysis, it is assumed that storage capacitors C1 and C2 are large. Specifically, it is assumed that the following conditions are met:

$$t_{rise} \ll \pi/2 * (\text{inductance of coil } L * \text{capacitance of capacitor } C1)^{1/2} \text{ and}$$

$$t_{fall} \ll \pi/2 * (\text{inductance of coil } L * \text{capacitance of capacitor } C2)^{1/2},$$

where $t_{rise}$ and $t_{fall}$ are the rise and fall times of the magnetic field generated by the stimulating coil L. Further, in this analysis, the component parasitics and losses in the circuit are ignored.

Under these conditions, the cTMS system induces approximately rectangular current pulses in the targeted body organ.

Referring to FIGS. 4A and 4B, in one embodiment, under the conditions specified above, graphs of positive and negative monophasic magnetic field pulses generated using the controllable pulse parameter transcranial magnetic stimulation circuit are shown. For this illustration, the ratio of the voltage across the capacitor C1 to the voltage across the capacitor C2 ($V_{C1}$:$V_{C2}$) is assumed to be 5:1. FIG. 4A depicts the generation of a positive magnetic field pulse 405, which is proportional to the current in the coil L.

When switch Q1 is switched to an on state 410, the resulting current ($I_L$) in the stimulating coil L increases at a rate of $dI_L/dt=V_{C1}/(\text{inductance of coil } L)$, as shown by waveform 416 in plot 415. Since capacitor C1 is very large, $V_{C1}$ stays approximately constant. After rise time $t_{rise}$, which is set by the operator by choosing when to turn Q1 on and off, switch Q1 is switched to an off state forcing the current $I_L$ in the stimulating coil L to commutate to capacitor C2 via the diode D2. While diode D2 is on, switch Q2 can be either on or off (referred to as a "don't care state" of the switch, and indicated with "x" symbols in the switch state waveforms). Since a negative voltage $-V_{C2}$ is now applied across the stimulating coil L, the stimulating coil current $I_L$ starts to decrease at a rate of $-V_{C2}/(\text{inductance of coil } L)$ as shown by waveform 417 in plot 415. The coil current $I_L$ decays to zero in fall time $t_{fall}$, where $t_{fall}$:$t_{rise}=V_{C1}$:$V_{C2}$. Under ideal conditions, all the energy transferred from capacitor C1 to the stimulating coil L, which is equal to $(\text{inductance of coil } L)*I_Lpk2/2$, is returned to capacitor C2, where $I_Lpk$ is the peak current in the coil L. Of course, as will be understood by those of ordinary skill in the art, losses will arise under ordinary (i.e., non-ideal) conditions, resulting in somewhat less than this amount of energy being transferred. This energy can be transferred back to capacitor C1 and reused in a subsequent pulse, which makes this strategy effective for repetitive TMS (rTMS).

FIG. 4B depicts the generation of a negative magnetic field pulse, which is proportional to the current in the coil L as previously described. When switch Q2 is switched to an on state 425, the resulting current ($I_L$) in the stimulating coil L decreases at a rate of $dI_L/dt=-V_{C2}/(\text{inductance of coil } L)$, as shown by waveform 429 in plot 430. After rise time $t_{rise}$, which is chosen by the operator, switch Q2 is switched to an off state forcing the current $I_L$ in the stimulating coil L to commutate to capacitor C1 via the diode D1. While diode D1 is on, switch Q1 can be either on or off (referred to as a "don't care state" of the switch, and indicated with "x" symbols in the switch state waveforms). Since a positive voltage $V_{C1}$ is now applied across the stimulating coil L, the stimulating coil current $I_L$ starts to increase at a rate of $V_{C1}/(\text{inductance of coil } L)$ as shown by waveform 428 in plot 430.

Figure 5A:
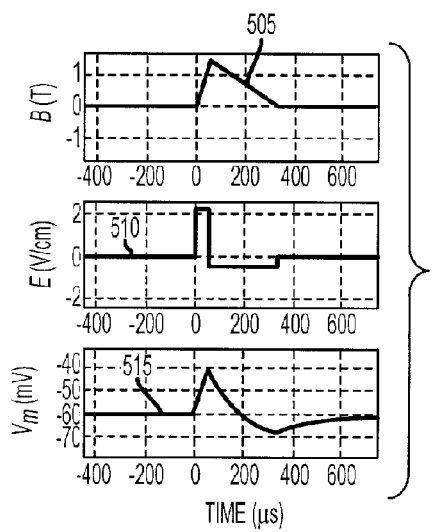
FIG. 5A shows illustrative waveforms of a monophasic magnetic field pulse (B), an associated electric field (E), and neuronal membrane voltage ($V_m$) induced in the brain by a controllable pulse parameter transcranial magnetic stimulation system, according to one embodiment of the disclosed subject matter.
Figure 5B:
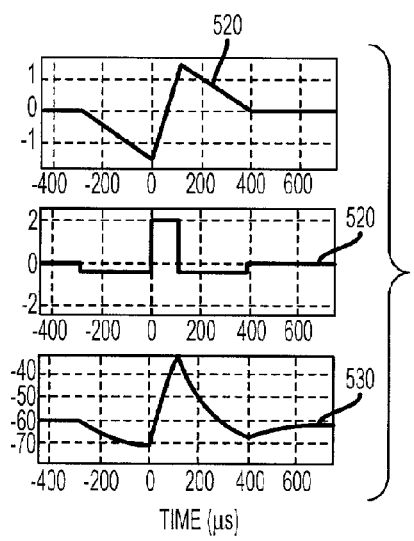
FIG. 5B shows illustrative waveforms of a biphasic magnetic field (B), an associated electric field (E), and neuronal membrane voltage ($V_m$) induced in the brain by a controllable pulse parameter transcranial magnetic stimulation system, according to one embodiment of the disclosed subject matter.

When the cTMS system is operated in monophasic magnetic pulse mode, as shown in FIG. 5A, the energy exchange between the storage capacitors C1 and C2 is implemented using charger circuit 210 to transfer energy from capacitor C2 to C1, or from capacitor C1 to C2 between pulses. When the cTMS system is operated in biphasic magnetic pulse mode, as shown in FIG. 5B, the energy exchange between the storage capacitors C1 and C2 is implemented by having a negative magnetic pulse precede a positive magnetic pulse. The energy from the storage capacitor C1 at the beginning of the pulse is returned to the storage capacitor C1 by the end of the pulse. The capability to operate in both monophasic and biphasic magnetic pulse modes enables optimization of the pulse type for specific research and clinical applications of the cTMS system.

Referring to FIG. 5A, in one embodiment, illustrative monophasic waveforms of a magnetic field pulse (B) 505, an electric field (E) 510, and a neuronal membrane voltage ($V_m$) 515, induced in the brain by the controllable pulse parameter transcranial magnetic stimulation system are shown.

As previously described, during a medical treatment, the stimulating coil L is positioned proximate to a patient's head. Adjustable current pulses are passed through the stimulating coil L and cause the stimulating coil L to generate adjustable magnetic field pulses. The adjustable magnetic field pulses induce adjustable electric field pulses which, in turn, induce adjustable current pulses in the patient's brain. The induced adjustable current pulses in the patient's brain result in voltage change on the neuronal membrane that can be measured.

The waveforms shown in FIG. 5A are produced by the current $I_L$ (plot 405) in the stimulating coil L shown in FIG. 4A. As previously described, the magnetic field B (plot 505) is proportional to the current $I_L$ in the stimulating coil L, and thus also has a triangular shape. The induced electric field E (plot 510) is proportional to the magnetic field rate of change (dB/dt), and correspondingly has a rectangular shape, rather than the cosine shape of existing TMS systems. Different rising and falling slopes of the magnetic field B (plot 505) result in different magnitudes of the positive and negative phases of the induced electric field E (plot 510), respectively. As previously described, the rate of change of the coil current (dIddt) and, therefore, the rate of change of the magnetic field (dB/dt) is proportional to the voltage across the coil L. The voltage across the coil L is equal to the voltage of the capacitor to which the coil is connected. Therefore, the ratio of peak positive to negative electric field E is $V_{C_1}:V_{C_2}$. This is true in general, even when the circuit non-idealities are considered. Since the induced electric field pulse has a rectangular shape, and due to the neuronal membrane capacitance, the neuronal membrane voltage ($V_m$) follows a decaying exponential curve characterized by the membrane time constant, as shown by plot 515. If the neuronal membrane is depolarized (i.e., made more positive) by more than approximately 15 mV relative to its resting potential (−60 to −70 mV), the neuron is likely to produce an action potential (i.e., to fire).

Referring to FIG. 5B, in one embodiment, illustrative waveforms of a biphasic magnetic field (B) 520, and the associated electric field (E) 525 and neuronal membrane voltage ($V_m$) 530 induced in the brain by the controllable pulse parameter transcranial magnetic stimulation system are shown. Although the magnetic field B of plot 520 is biphasic with symmetric positive and negative phases, the induced electric field (plot 525) has a large positive amplitude and a comparatively small negative amplitude, since the rate of change of the rising magnetic field is much larger than the rate of change of the falling magnetic field. As a result (plot 530), the depolarization amplitude (as the neuronal membrane is made more positive) is larger than the hyperpolarization amplitude (as the neuronal membrane is made more negative). This example demonstrates how the cTMS system can produce predominantly unipolar electric field pulses and neuronal membrane voltage changes with biphasic magnetic pulses. In contrast, conventional sinusoidal biphasic magnetic pulses induce electric fields and neuronal membrane voltage changes that are bipolar (i.e., have approximately equal amplitudes of the positive and negative phases of the electric pulse). Biphasic magnetic pulses are more electrically efficient and produce less coil heating than monophasic magnetic pulses. Further, TMS biphasic magnetic pulses can be used inside a magnetic resonance imaging (MRI) scanner, since the torque on the wire loops of the stimulating coil L in the strong magnetic field of the scanner averages to approximately zero. In contrast, monophasic pulses cannot be used in an MRI scanner, since the average toque on the coil loops is non-zero, resulting in high mechanical stress in the coil that can damage the coil.

Figure 6:
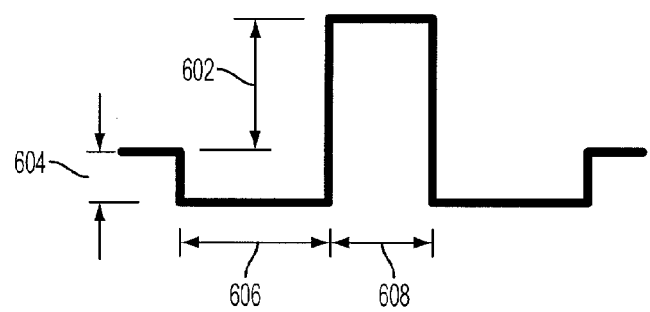
FIG. 6 is an illustrative waveform depicting user-adjustable pulse parameters, according to one embodiment of the disclosed subject matter.

Referring to FIG. 6, in one embodiment, an illustrative waveform depicting user-adjustable pulse parameters is shown. The user-adjustable parameters include: induced positive electric field amplitude (A) 602 (which corresponds to the intensity setting on conventional TMS systems), the pulse width of the positive phase (PW$^+$) 608, the induced negative electric field amplitude (M*A=($V_{C2}/V_{C1}$)*A) 604, which is specified through M, the ratio of negative to positive capacitor voltage, and the frequency of the pulse repetition ($f_{train}$). For biphasic operation, the duration of an initial negative electric field phase (PW$^−$) 606 can also be specified (PW$^−$=PW$^+$/2M for symmetric negative side lobes of the pulse).

Figure 7:
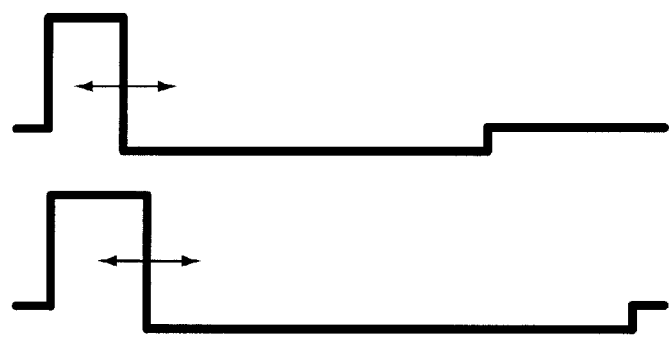
FIG. 7 shows illustrative waveforms of approximately rectangular induced electric field pulses with pulse widths adjustable over a continuous range of values, generated by a controllable pulse parameter transcranial magnetic stimulation circuit, according to one embodiment of the disclosed subject matter.

Referring to FIG. 7, in one embodiment, illustrative waveforms of approximately rectangular, predominantly unipolar current pulses with adjustable pulse width are shown. Control over the pulse width (PW$^+$) of the induced electric field pulse is accomplished by controlling the on and off timing of the semiconductor switches Q1 and Q2.

Figure 8:
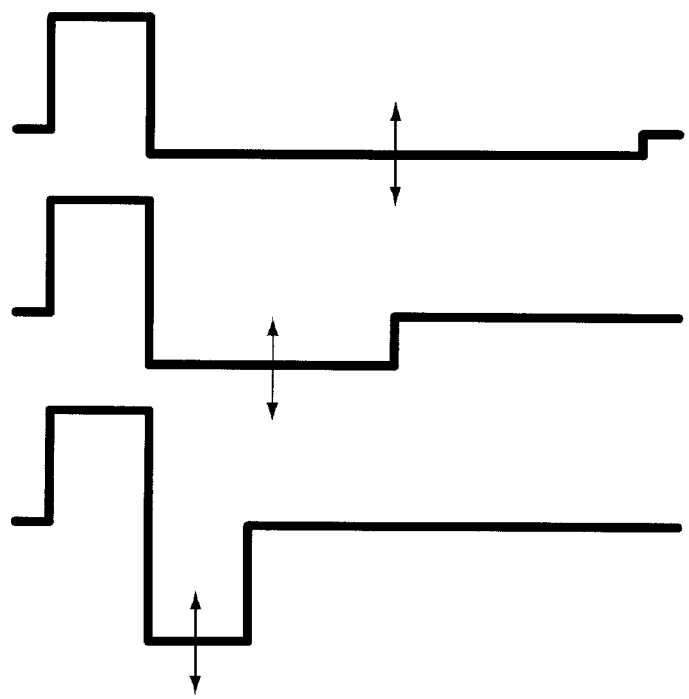
FIG. 8 shows illustrative waveforms of approximately rectangular induced electric field pulses with bidirectionality adjustable over a continuous range, generated by a controllable pulse parameter transcranial magnetic stimulation circuit, according to one embodiment of the disclosed subject matter.

Referring to FIG. 8, in one embodiment, illustrative waveforms depicting user-adjustable degree of bidirectionality of approximately rectangular electric field pulses are shown. Control over the degree of bidirectionality is accomplished by adjustment of the voltages of energy storage capacitors C1 and C2 relative to each other.

Figure 9:
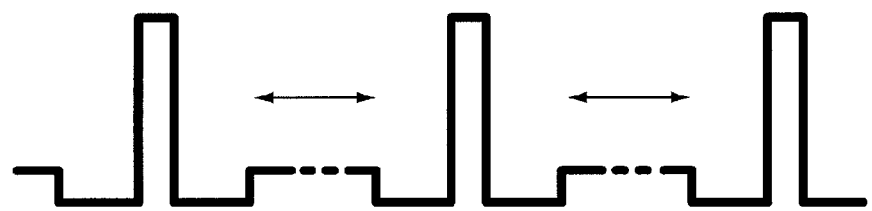
FIG. 9 is an illustrative waveform of repetitive TMS with predominantly unipolar induced electric field pulses, with adjustable pulse repetition frequency, according to one embodiment of the disclosed subject matter.

FIG. 9 shows an illustrative waveform of rTMS with a predominantly unipolar induced electric field. Computer simulations of a representative implementation of the cTMS system (FIG. 10) indicate that the cTMS pulses can induce membrane depolarization and hyperpolarization equal to that of commercial monophasic stimulators at only 16-18% of the power dissipation. This results in a reduction of power supply demands, heating, noise, and component size, and enables the cTMS system to produce high-frequency rTMS with predominately unipolar induced electric fields.

Figure 10:
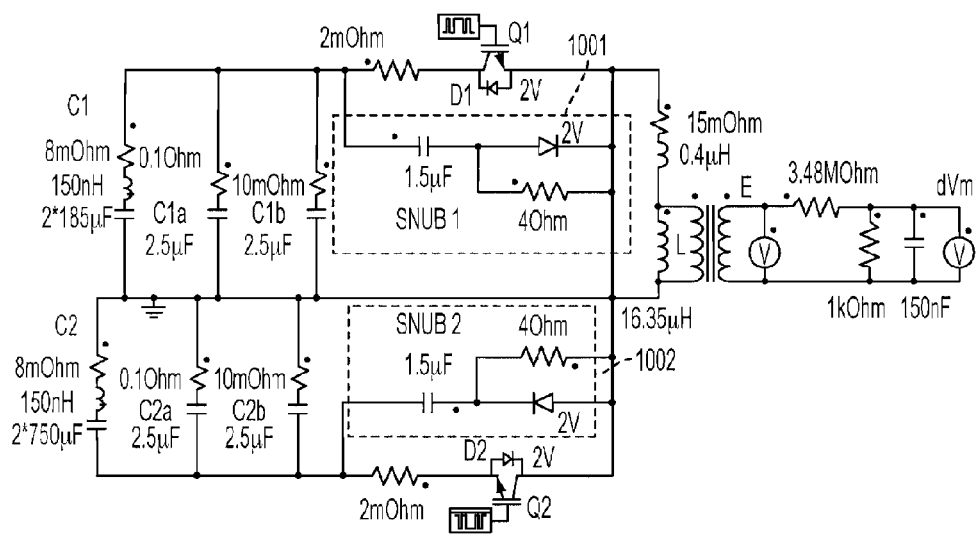
FIG. 10 is an illustrative simulation circuit for producing controllable pulse parameter transcranial magnetic stimulation, in accordance with the disclosed subject matter.

The cTMS system described in the disclosed subject matter was simulated and compared to existing TMS systems. A schematic of the cTMS simulation circuit is shown in FIG. 10. Further, a set of pulse performance metrics, i.e. performance figures, used to evaluate the efficiency of cTMS pulses compared to conventional pulse configurations of commercial TMS systems is shown in FIG. 11. The values were derived from computer simulations using PSIM circuit simulation software (available from Powersim Inc.) and the simulation circuit shown in FIG. 10.

Figure 12A:
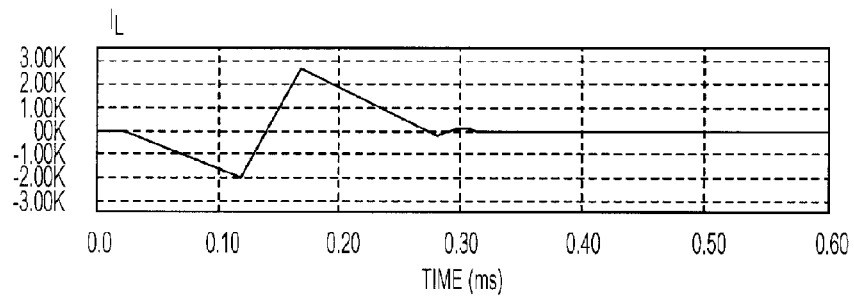
FIG. 12A shows an illustrative waveform of a coil current produced by the simulation circuit of FIG. 10.
Figure 12B:
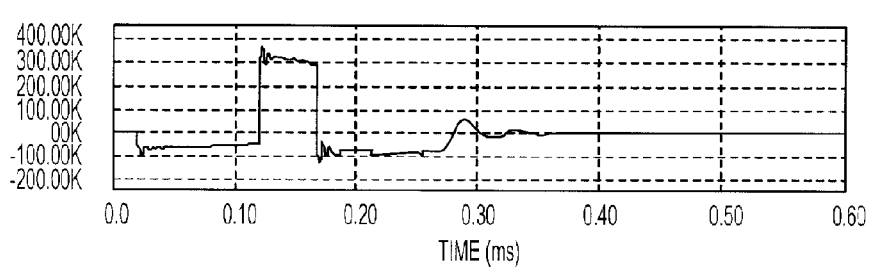
FIG. 12B shows an illustrative waveform of a peak induced electric field produced by the simulation circuit of FIG. 10.
Figure 12C:
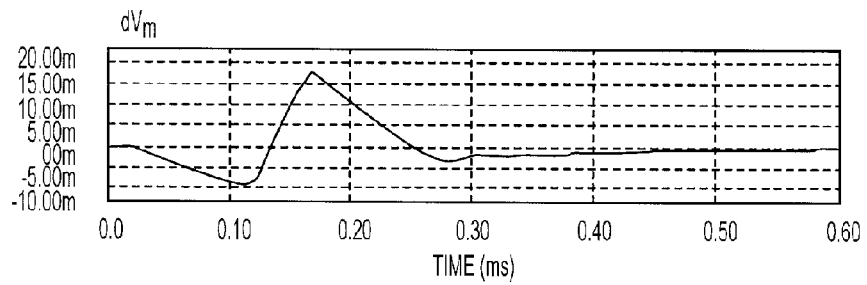
FIG. 12C shows an illustrative waveform of a neuronal membrane voltage change produced by the simulation circuit of FIG. 10.

Realistic component values are used. As previously described, snubber circuits 1001 and 1002 are added across the semiconductor devices Q1 and Q2, snubber capacitors C1a and C1b are added across the capacitor bank C1, and snubber capacitors C2a and C2b are added across capacitor bank C2 to handle transient energy. Waveforms showing the coil current $I_L$, peak induced electric field (E), and estimated neuronal membrane voltage change (d$V_m$) corresponding to the cTMS configuration shown in FIG. 10 are shown in FIGS. 12A, 12B, and 12C, respectively.

To allow a valid comparison of the pulse shape efficiency, all configurations use a model of Magstim "figure-of-8", air-core coil (L=16.4 µH), parasitic series resistance and inductance of 25 mΩ and 0.6 µH and neuronal membrane time constant τm=150 µs. The actual Neuronetics 2100 and Medtronic MagPro X100 systems use different coils than the Magstim figure-of-8 used in the comparison. Therefore, for the calculations for these systems, the capacitance was adjusted to match their typical pulse periods of approximately 200 and 270 µs, respectively, for the given 16.4 µH coil, because the objective is to compare the waveform efficiency rather than the actual commercial systems and coils.

To account for the higher efficiency of ferromagnetic (iron) core coils, standard with the Neuronetics 2100 machine, the total energy loss per pulse and the load integral (proportional to coil heating) are recalculated for an iron core coil, as indicated in FIG. 11. The iron core proportionally increases the efficiency of all pulse configurations, and can be used with the cTMS system to improve efficiency. Four representative cTMS pulse configurations are simulated (see columns cTMS1-cTMS4 of FIG. 11). For biphasic cTMS pulses (cTMS2-cTMS4), the duration of the initial negative phase was set to $PW^- = PW^+/2M$. The amplitude of the commercial device (Magstim, MagPro, Neuronetics) pulses is adjusted to produce equal neuronal membrane depolarization of $\Delta V_m = 18$ mV, which is 20% above the assumed neuronal firing threshold of 15 mV depolarization. The amplitude and pulse width of the cTMS pulse configuration are also adjusted to produce identical neuronal membrane depolarization of $\Delta V_m = 18$ mV.

FIG. 11 shows that the cTMS system can produce predominantly unipolar neuronal membrane potential change with both monophasic (cTMS1) and biphasic (cTMS2-TMS4) magnetic field pulses. For example, the cTMS2 pulse configuration yields a membrane hyperpolarization/depolarization ratio of 0.27, which is comparable to that of the Magstim 200 and MagPro X100 (monophasic mode), while dissipating only 16% and 18% of the energy, respectively. The energy dissipation per pulse was calculated using the following equation:

$$\Delta W_C = \left( \frac{1}{2} \sum_{\substack{\text{sum of all} \\ \text{capacitors} \\ \text{before pulse}}} Ci(V_{Ci})^2 \right) - \left( \frac{1}{2} \sum_{\substack{\text{sum of all} \\ \text{capacitors} \\ \text{after pulse}}} Ci(V_{Ci})^2 \right),$$

where Ci refers to each capacitor in the stimulator power electronics, and where capacitor Ci has voltage $V_{Ci}$.

Further, coil heating (proportional to the load integral $I_{L2}dt$) with the cTMS2 pulse is only 32% and 36% that of the Magstim 200 and MagPro X100, respectively. cTMS is able to achieve a total energy dissipation $\Delta W_C$ comparable to efficient biphasic systems, such as the Neuronetics 2100, with 8-59% less coil heating (load integral) while adding the previously unavailable functionalities of control over the induced electric field pulse width, degree of bidirectionality, approximately rectangular shape, and predominantly unipolar electric field pulses. It should be noted that for very brief, high-intensity rectangular pulses (cTMS4), the coil heating decreases dramatically, while the total energy dissipation increases slightly. This is due to energy loss in the cTMS snubber circuits, which is proportional to the square of the capacitor voltage. However, since it is easier to cool the snubber circuits, which are inside the power electronics enclosure, than the coil, the reduced coil heating of brief, rectangular, high-voltage pulses can be advantageous in high-power applications such as magnetic seizure therapy (MST) where coil heating is currently the bottleneck for pulse train duration. Finally, in this model we have not accounted for ferromagnetic core losses, which could be higher for briefer pulses.

When monophasic magnetic field pulses are generated, energy is transferred from capacitor C1 to C2, and has to be transferred back to C1 by the power supply before the subsequent pulse in repetitive TMS (rTMS) operation. However, if a biphasic magnetic pulse is used to produce a predominantly unipolar electric field pulse, as shown in FIG. 5B and FIG. 12A-C, energy is transferred from C2 to C1 and then back from C1 to C2 during the pulse. Thus, there is no need for rebalancing a large amount of energy between the capacitors before the subsequent pulse, except for "topping off" the capacitors to compensate for the energy dissipated in losses during the pulse, as is the case in conventional biphasic TMS systems. With both monophasic and biphasic cTMS magnetic field pulses, the energy returning from the coil after each pulse is recycled, unlike that in conventional monophasic converters, which is dissipated in a resistor. However, compared to cTMS biphasic magnetic field pulses, monophasic magnetic field pulses require higher power capability of the cTMS power supply circuit that moves charge between the two capacitors.

Thus, the cTMS system is particularly well suited to generate high-frequency trains of predominantly unipolar electric field pulses. Using the results in FIG. 11, the unipolar rTMS power dissipation and coil heating of cTMS can be compared to that of conventional monophasic stimulators. The cTMS2 configuration is 5-6 times more efficient and has about three times less coil heating than the Magstim 200 and MagPro X100 while producing the same neuronal depolarization and comparable hyperpolarization/depolarization ratio. For a pulse train frequency of 10 Hz, the Magstim 200, MagPro X100, and cTMS2 pulse configurations described in FIG. 11 dissipate 1600, 1420, and 260 W, respectively, while the coil dissipation, assuming coil resistance of 10 mfl, is 248, 222, and 80 W, respectively. If an iron-core coil is used, cTMS energy dissipation and coil heating can be further reduced to about 65 and 20 W, respectively. Therefore, with its substantially lower power dissipation and coil heating, the cTMS system can enable rTMS with predominantly unipolar electric field pulses. Recent research has indicated that rTMS with predominantly unipolar electric field pulses may have a stronger modulating effect on brain function, and, therefore, could be a more effective therapeutic intervention.

Figure 13A:
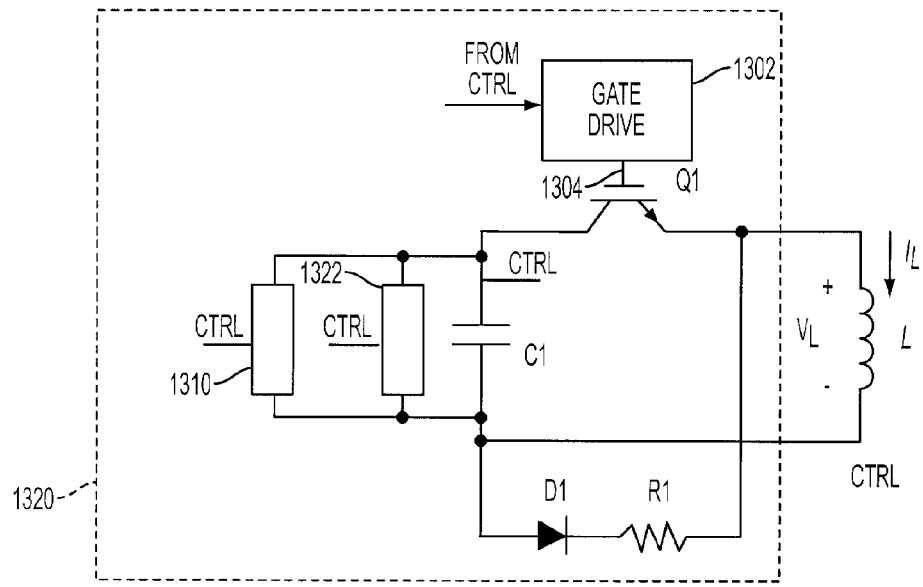
FIG. 13A is an illustrative block diagram of power electronics circuitry for a controllable pulse parameter transcranial magnetic stimulation system, according to another embodiment of the disclosed subject matter.
Figure 13B:
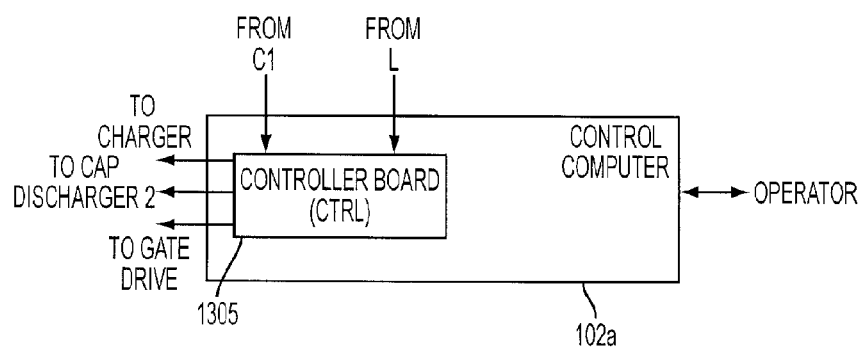
FIG. 13B is an illustrative block diagram of another embodiment of the control computer electronics for the controllable pulse parameter transcranial magnetic stimulation system.

Referring to FIGS. 13A and 13B, in an alternative embodiment, illustrative block diagrams of power electronics and a control computer system 102a for a controllable pulse parameter transcranial magnetic stimulation (cTMS) system are shown. The cTMS system includes a cTMS circuit 1320 for driving a stimulating coil L. The cTMS circuit 1320 includes energy storage capacitor (or bank of capacitors) C1, controllable semiconductor switch Q1, a gate drive 1302, charger 1310, capacitor discharger 1322, diode D1, and resistor R1. The cTMS system further includes a digital data processing device, such as control computer system 102a, which includes a controller board 1305.

This particular embodiment enables adjustment of the amplitude and the pulse width of the induced electric field over a continuous range of values, and the induced electric field pulses have an approximately rectangular shape. The semiconductor switch Q1 is implemented with an IGBT, which unlike an SCR, can be turned off from a gate terminal 1304. Further, the diode D1 and the energy dissipation resistor R1 are connected across the TMS coil L, to provide a discharge path for the coil current when Q1 is turned off. The energy storage capacitor C1 is larger than those used in conventional TMS stimulators to provide a wider range of pulse width control and approximately rectangular induced electric field pulses.

Similar to the cTMS circuit described in connection with FIGS. 2A, 2B, and 3A, the cTMS circuit 1320 shown in FIG. 13A is controlled by the controller board 1305 shown in FIG. 13B, which resides in the control computer 102a. Through the controller board 1305, the operator specifies the voltage of capacitor C1, which determines the amplitude of the induced electric field. The operator also specifies the on time and the off time of switch Q1, which determine the pulse timing and the pulse width ($PW^+$).

Figure 14:
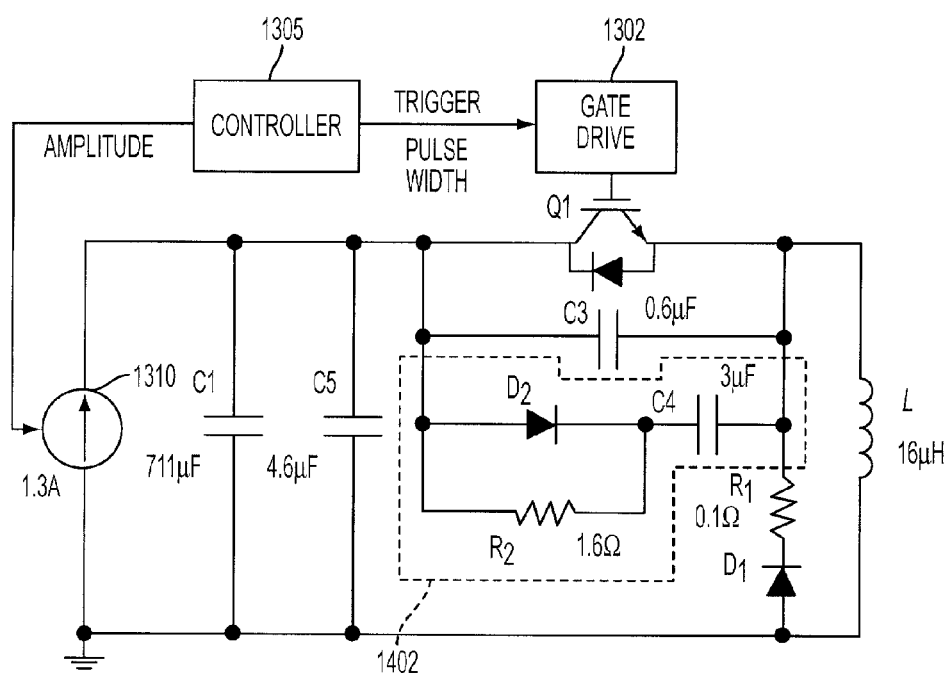
FIG. 14 is an illustrative schematic of a controllable pulse parameter transcranial magnetic stimulation circuit, according to another embodiment of the invention.

Referring to FIG. 14, in another embodiment, a schematic diagram of the cTMS circuit is shown. Stray inductance in the critical high-current paths of the circuit can cause power loss and voltage spikes during turn-off of switch Q1, which can cause component damage, as previously discussed. Therefore, the wiring and component locations in the cTMS circuit are arranged to reduce and/or minimize the stray inductance. However, stray inductances cannot be completely eliminated. Therefore, the cTMS circuit includes a number of snubber components. The snubber components assist the coil current commutation between the switch Q1 and the diode D1 and inhibits and/or prevents voltage overshoots and energy dissipation in the semiconductor switch Q1. A snubber capacitor or combination of capacitors C5 is mounted between the collector terminal of switch Q1 and the anode terminal of diode D1 to prevent the collector voltage from spiking during switch Q1 turn-off as a result of parasitic inductance of the capacitor bank C1 and the connecting wires. A capacitor C3 is mounted between the collector and emitter terminals of the switch Q1 to suppress high-voltage spikes across the terminals of switch Q1. A snubber circuit 1402, which includes diode D2, capacitor C4, and resistor R2, transiently absorbs the current flowing through the coil L when Q1 is turned off. This supports the current commutation to diode D1 and resistor R1, as previously discussed.

The energy storage bank of capacitors C1 comprises six 118 µF (average measured value) oil-filled pulse capacitors. The bank of capacitors C1 is charged by a Magstim Booster Module Plus (The Magstim Co., Whitland, UK) and a Magstim capacitor voltage control circuit. The semiconductor switch Q1 is a 4500 Volt/600 Amp (direct current rating) IGBT module from Powerex, Inc. (Youngwood, Pa.). The IGBT (switch Q1) is controlled with a high-voltage optically-isolated gate drive 1302 by Applied Power Systems, Inc. (Hicksville, N.Y.). The controller board 1305 sends triggering pulses to the gate drive 1302. As previously described, the pulse width is set by the operator. The diode D1 is implemented with two series-connected, fast 1800 Volt/102 Amp (direct current rating) diodes by Semikron GmbH (Nuremberg, Germany). The snubber capacitors C3-05 are high-voltage, high-current polypropylene film and paper film/foil capacitors. The snubber diode D2 includes three series-connected fast-recovery 1200 Volt/60 Amp (direct current rating) diodes from International Rectifier (El Segundo, Calif.). The stimulating coil L is a custom-made Magstim 5.5 cm mean diameter round coil with an inductance of 16 µH.

The cTMS circuit of FIG. 14 was tested with capacitor voltages of up to 1650 Volts, and peak coil currents of up to 7 kA. The peak intensity (i.e. amplitude of the electric field) of the cTMS system is equal to that of commercial Magstim Rapid stimulators. Unlike conventional stimulators, however, the cTMS system of the disclosed subject matter allows pulse width control with a range between 5 µs and 160 µs.

The electric field induced by the cTMS system was estimated with a single-turn 5 cm diameter search coil placed two centimeters from the face of the cTMS coil L. The search coil was connected to a digitizing oscilloscope as well as to a first-order low-pass filter with 150 µs time constant, which outputs a scaled estimate of the neuronal membrane voltage waveform.

Figure 15A:
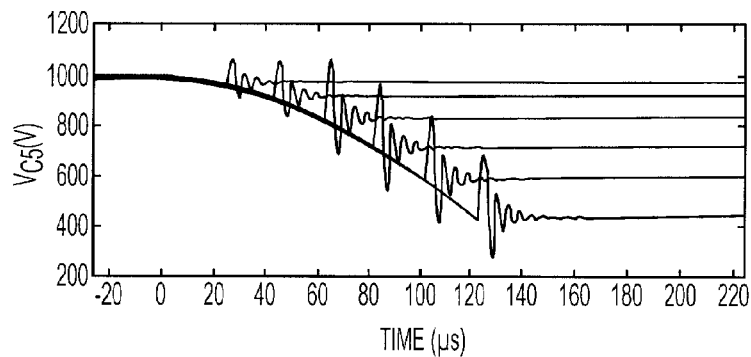
FIG. 15A shows illustrative waveforms of voltage across capacitor C5 for different pulse widths of the controllable pulse parameter transcranial magnetic stimulation circuit of FIG. 14.
Figure 15B:
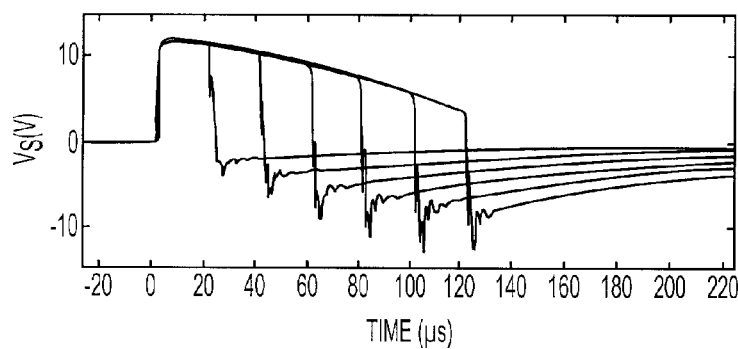
FIG. 15B shows illustrative waveforms of voltage induced in a search coil by the stimulating coil L for different pulse widths of the controllable pulse parameter transcranial magnetic stimulation circuit of FIG. 14.
Figure 15C:
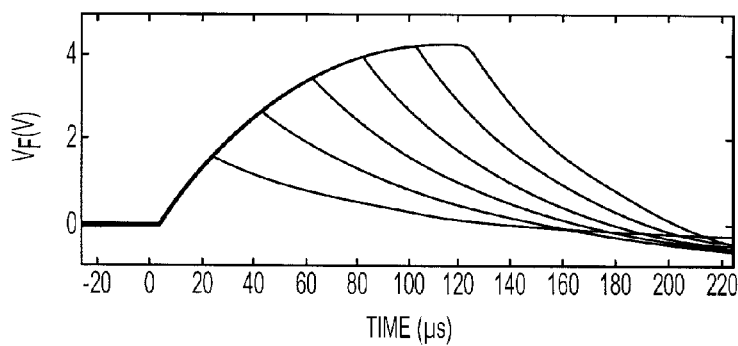
FIG. 15C shows illustrative waveforms of estimated shape of neuronal membrane voltage change for different pulse widths induced with the controllable pulse parameter transcranial magnetic stimulation circuit of FIG. 14.

Referring to FIGS. 15A-C, illustrative waveforms of measured capacitor C5 voltage (FIG. 15A), search coil voltage $V_S$ (proportional to the induced electric field, FIG. 15B), and the estimated shape of the neuronal membrane voltage ($V_F$) (FIG. 15C), which is determined by filtering the search coil voltage $V_S$ through a low-pass filter with 150 µs time constant, are shown. The waveforms show six different pulse widths (i.e., 20, 40, 60, 80, 100, and 120 µs). It can be seen in FIG. 15B that the induced pulses, which are proportional to the electric field, have approximately rectangular shape, especially for brief pulses (e.g., 20 µs pulse).

As expected, overshoot and high-frequency ringing are present on the capacitor C5 voltage (FIG. 15A) and search coil voltage (proportional to the electric field, FIG. 15B) during switch Q1 turn-off, due to stray inductance. However, these transients are suppressed to a safe level by the snubber circuits. In particular, the capacitor voltage overshoot does not exceed 7% of the initial capacitor voltage, and the voltage across the switch Q1 never exceeds approximately twice the initial capacitor voltage, and is thus well below the 4,500 V rating of the IGBT (Q1). These results indicate the feasibility of high coil current commutation through appropriate choice of semiconductor switches, switch gating, snubber design, and minimization of stray inductance.

The above described cTMS implementation can be used to compare the intrinsic efficiency of rectangular unipolar electric field pulses versus conventional unipolar cosine pulses. In order to emulate conventional monophasic magnetic field pulses, the cTMS implementation was reconfigured to use a smaller capacitor and switch Q1 was kept on until the coil current decayed to zero. The comparison of rectangular pulses used the same initial capacitor voltage, and the cTMS pulse width was adjusted to achieve the same estimated neuronal depolarization. The energy dissipation per pulse was calculated using the formula:

$$\Delta W_C = \left( \frac{1}{2} \sum_{\substack{\text{sum of all} \\ \text{capacitors} \\ \text{before pulse}}} Ci(V_{Ci})^2 \right) - \left( \frac{1}{2} \sum_{\substack{\text{sum of all} \\ \text{capacitors} \\ \text{after pulse}}} Ci(V_{Ci})^2 \right),$$

where Ci refers to each capacitor in the stimulator power electronics, and where capacitor Ci has voltage $V_{Ci}$.

Compared to conventional monophasic magnetic field pulses with rise times of 72 and 101 µs, the corresponding rectangular pulses dissipated 20 and 28% less energy, respectively. The cTMS circuit of FIG. 14 does not recycle pulse energy (pulse energy is dissipated in resistor R1 in FIG. 14), so this gain in efficiency comes solely from the rectangular pulse shape. With energy recycling, which is implemented in the circuit in FIG. 2 and FIG. 3, efficiency will be even higher, as discussed above.

Figure 16:
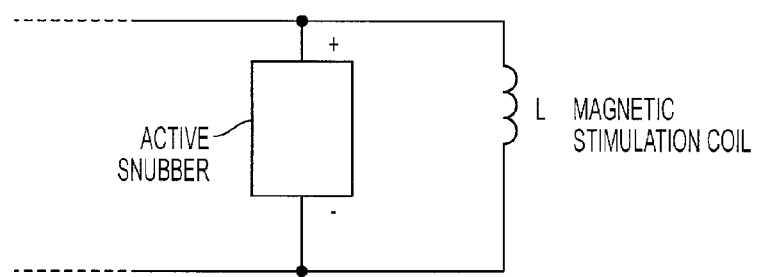
FIG. 16 is an illustrative schematic diagram of an active snubber circuit in parallel with a magnetic stimulation coil.

In FIG. 16 is shown an active snubber circuit connected in parallel with a magnetic stimulation coil L. The active snubber circuit can be used in any of the disclosed embodiments and others as illustrated in FIG. 16. For example, it can be used as the snubber circuit 226 in the embodiment of FIG. 2A.

Figure 17:
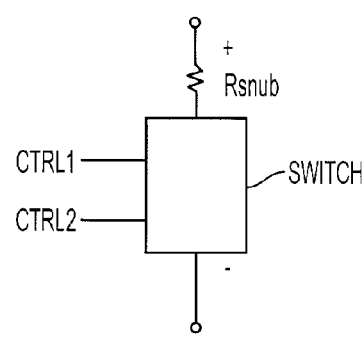
FIG. 17 is an illustrative schematic diagram of an active snubber circuit.

The active snubber circuit of FIG. 16 may include a non-inductive resistor Rsnub and at least two current-unidirectional switches (switch) as shown in FIG. 17. The value of the non-inductive resistor Rsnub may be chosen to provide critically damped, or overdamped, response of the resonance between the coil L inductance and the capacitance of the pulse generator switching node, i.e., the capacitance that appears in parallel with the coil L when the coil is disconnected from the energy storage capacitors C1 and C2. This switching node capacitance typically results from the capacitance of snubbers 222 and 223 and from the capacitance of switches Q1 and Q2 in FIG. 2A.

In embodiments, when CTRL1 is activated, current in a first direction is permitted to be established in Rsnub and when CTRL2 is activated, current in a second, reverse, direction is permitted to be established in Rsnub. Referring to FIG. 16, when an undesired resonance generates a positive voltage across coil L, for example after a pulse is generated by the pulse generator circuit (not shown), the activation of CTRL1 will cause dissipation of the energy in Rsnub. For example, the CTRL1 can be activated at any time during a negative phase for the electric field pulse when the coil current is ramping down toward zero and as soon as the coil voltage becomes positive due to resonance, the active snubber will permit current to flow through Rsnub and dissipate the energy.

In a similar manner, when CTRL2 is activated, current in the second direction is permitted to be established in Rsnub. When an undesired resonance generates a negative voltage across coil L, for example after a pulse is generated by the pulse generator circuit (not shown), the activation of CTRL2 will cause dissipation of the energy in Rsnub. For example, the CTRL2 can be activated at any time during a positive phase of the electric field pulse when the coil current is ramping up toward zero and as soon as the coil voltage becomes negative due to resonance, the active snubber will permit current to flow through Rsnub and dissipate the energy.

Figure 18A:
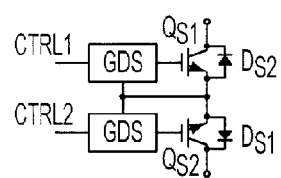
FIGS. 18A-18E are illustrative schematic diagrams of switch implementations in an active snubber circuit.
Figure 18B:
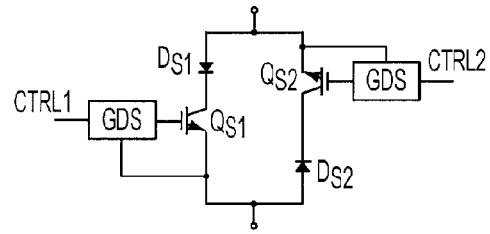
Figure 18C:
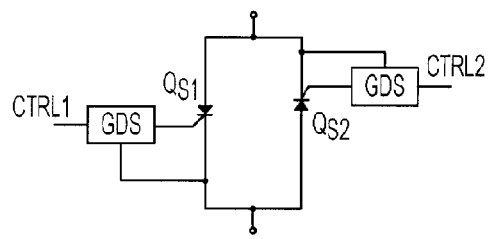
Figure 18D:
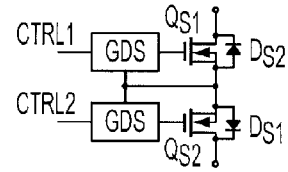
Figure 18E:
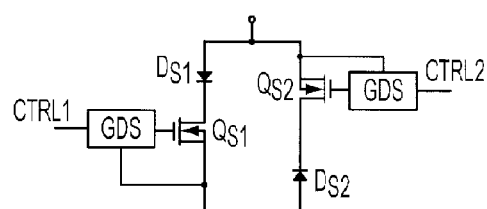

Different circuit embodiments for the switches included in the active snubber circuit of FIG. 17 are shown in FIGS. 18A-18E. The switches can be implemented, for example, with IGTB ($QS_1$, $QS_2$) and diode ($DS_1$, $DS_2$) combinations, as shown in FIGS. 18A-18B, and/or SCRs ($QS_1$, $QS_2$), as shown in FIG. 18C, and/or MOSFET ($QS_1$, $QS_2$) and diode ($DS_1$, $DS_2$) combinations, as shown in FIGS. 18D-18-E. In each of these cases, CTRL1 and CTRL2 signals are generated by a controller similar to that described with regard to the embodiment of FIG. 2B, modified by providing appropriate control signals for CTRL1 and CTRL2. Also illustrated in FIGS. 18A-18E are gate drivers, as indicated at GDS, if and as appropriate for the type of switch employed.

Figure 19:
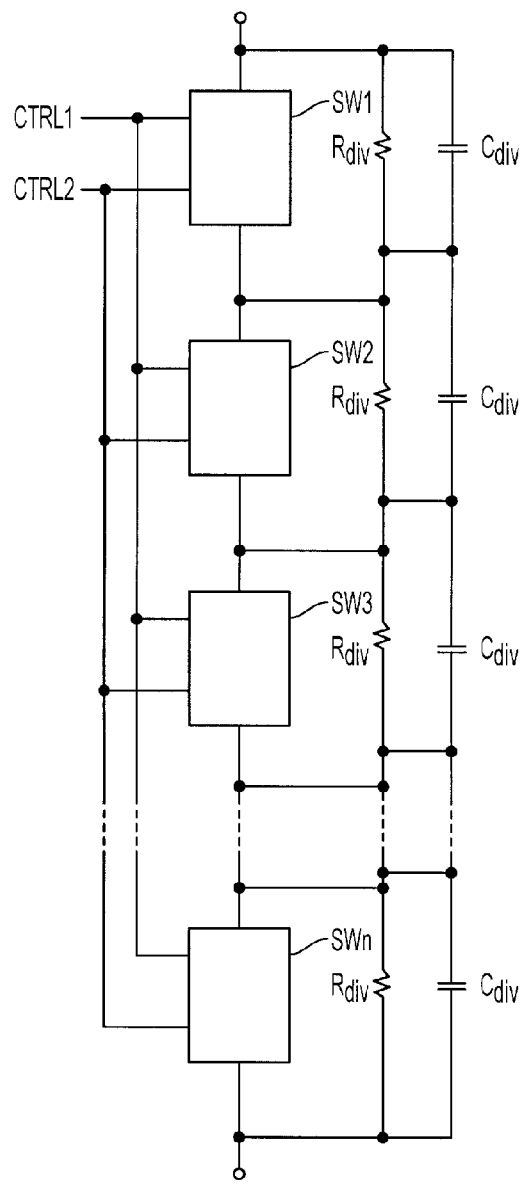
FIG. 19 is an illustrative schematic diagram of an active snubber circuit with switches connected in series.

The Q1, Q2 switch functions (responsive to CTRL1 and CTRL2) can also be implemented with components with lower voltage rating than the peak value of the voltage across the coil L by connecting a plurality n of switches (SW1-SWn) in series, as shown in FIG. 19. A resistor-capacitor voltage divider ladder ($R_{div}$-$C_{div}$) including n resistors $R_{div}$ and n capacitors $C_{div}$ can be installed to force equal voltage drops on all n switch stages (SW1-SWn). Rdiv can also be implemented with non-linear resistance elements, such as transient voltage suppressor (TVS) diodes. The control signals CTRL1 and CTRL2 are applied to the same effect as described above. In embodiments, each of SW1 can assume any of the configurations of FIGS. 18A-18E or others.

Figure 20:
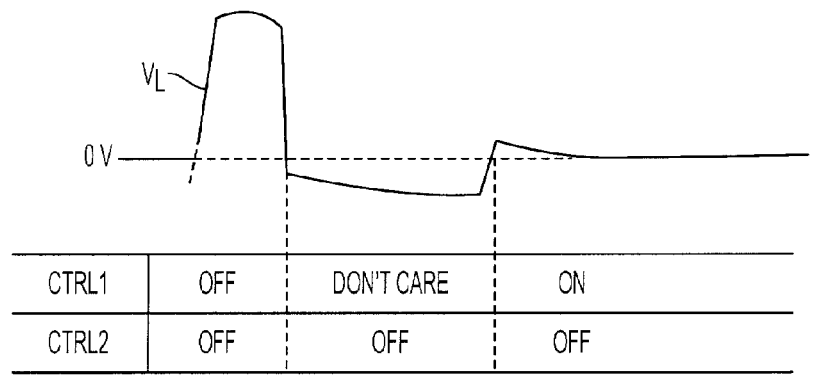
FIG. 20 shows an illustrative schematic of activating a positive current conducting active snubber switch.
Figure 21:
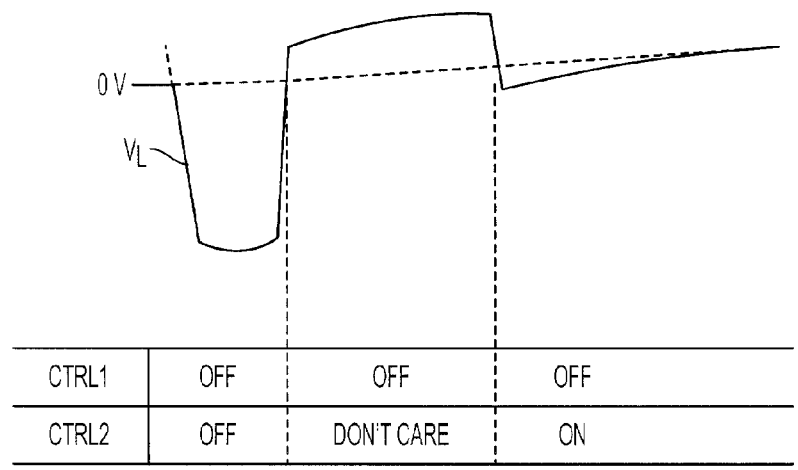
FIG. 21 shows an illustrative schematic of activating a negative current conducting active snubber switch.

FIGS. 20 and 21 illustrate activating a positive and a negative current conducting active snubber switch, respectively. In operation, if a TMS pulse ends with a negative voltage phase (voltage $V_L$ applied to the coil L of FIG. 16 or similarly in other embodiments), then the positive-current conducting snubber switch is activated by the controller (CTRL1—ON) anytime during the voltage negative phase (FIG. 20). When the voltage $V_L$ goes positive at the end of the negative phase, due to resonance of the coil L with the capacitance of the pulse generator switching node, current will start to flow in the active snubber. Thus, the energy in the coil L and in the capacitance of the pulse generator switching node will be dissipated in Rsnub. If, on the other hand, the TMS pulse ends with a positive voltage $V_L$ phase, then the negative-current conducting snubber switch is activated by the controller (CTRL2—ON) anytime during the $V_L$ positive phase (FIG. 21). When $V_L$ goes negative after the end of the positive phase, due to resonance of the coil L with the capacitance of the pulse generator switching node, current will start to flow in the active snubber. Thus, the energy in the coil L and in the capacitance of the pulse generator switching node will be dissipated in Rsnub. Although the discussion of FIGS. 20 and 21 assumed a biphasic pulse sequence, it should be clear that the snubber can be used for the control of transients in monophasic pulses or any other pulse sequences with appropriate configurations. For example, to control transients of a single polarity, a single control signal and switch may be used. Also, although Rsnub is described above as critically, or over damped, it is possible for it to be under damped. In the case of underdamping, oscillating may be tolerated or additional switching cycles may be provided to pass current through Rsnub in both directions during a parasitic oscillation event.

Figure 22:
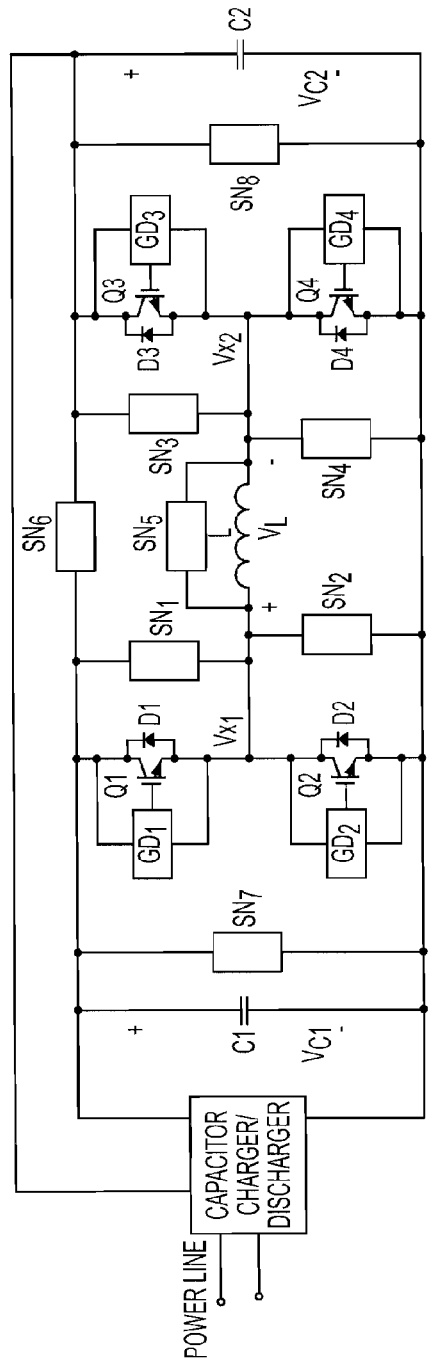
FIG. 22 is an illustrative schematic diagram of another embodiment of the power electronics circuitry for the controllable pulse parameter transcranial magnetic stimulation circuit.

Referring to FIG. 22, an illustrative schematic diagram of an alternative controllable pulse parameter transcranial magnetic stimulation circuit for driving the stimulation coil L is shown. The controllable pulse parameter transcranial stimulation circuit for driving the stimulation coil L includes energy storage capacitor (or bank of capacitors connected in series and/or parallel) C1, energy storage capacitor (or bank of capacitors connected in series and/or parallel) C2, four (4) controllable current-unidirectional semiconductor switches Q1-Q4, (Q1 and Q2 connected to C1 and Q3 and Q4 connected to C2), four (4) gate drives GD1-GD4, controlled by the system controller, for turning switches Q1-Q4, on and off, respectively, and a capacitor charger/discharger (shown connected to a power source such as voltage mains). The circuit additionally includes four (4) diodes D1-D4 connected in anti-parallel with respective controllable semiconductor switches Q1-Q4, as well as snubber circuits $SN_1$-$SN_8$. Note that any and all of the snubber circuits $SN_1$-$SN_8$ is optional and provided as required for controlling transients and reducing switching losses as desired.

Referring to FIG. 22, an operator may control the cTMS system using control computer electronics 110, shown in FIG. 1. For example, the operator may select cTMS system operation with monophasic magnetic pulses and a desired set of induced electric field pulse parameters, such as the pulse amplitude (A), width of positive pulse phase (PW$^+$), and the frequency of pulse repetition via a graphical user interface.

The controller board is in communication with and controls the charger/discharger, and also receives data from the energy storage capacitors C1 and C2, and the stimulating coil L.

The charger/discharger may charge the energy storage capacitor C1 to a positive voltage $V_{C1}$ (set by the operator), and the energy storage capacitor C2 also to a positive voltage $V_{C2}$ (set by the operator). This is in contrast to the embodiments described above with reference to FIGS. 2A and 3A. The charger/discharger may charge the capacitors from the mains we well as transfer energy between the two capacitors C1 and C2. The charger/discharger can also dissipate energy from C1 to C2, for example in the form of heat. The positive capacitor voltages $V_{C1}$ and $V_{C2}$ are independently selectable via the controller and implemented through the charger/discharger.

The stimulating coil L is connected to capacitor C1 via semiconductor switches Q1 and Q2 and diodes D1 and D2, and is connected to capacitor C2 via semiconductor switches Q3 and Q4 and diodes D3 and D4. The controller supplies separate sets of timing pulses with adjustable widths (set by the operator) to the first, second, third and fourth gate drives ($GD_1$-$GD_4$), which use the timing pulses to produce separate sets of voltage pulses with adjustable widths.

The voltage pulses from the controller board are used to switch the semiconductor switches Q1-Q4 to an on or an off state, and the anti-parallel connected diodes D1-D4 conduct current depending on the state of switches Q1-Q4 and the coil current L.

The semiconductor switches Q1-Q4 and diodes D1-D4 are connected to the stimulation coil L in such a way as to be able to apply to a first terminal Vx1 of the coil L a voltage $V_{C1}$ or 0, and the second terminal Vx2 to a voltage $V_{C2}$ or 0. Thus, the coil voltage $V_L$ could have any of the following values applied across it (reference polarity as indicated in FIG. 22 being positive on the left and negative on the right): 0, $V_{C1}$, $-V_{C2}$, or $V_{C1}$-$V_{C2}$. The switches Q1-Q4 are turned on and off by the controller so that $V_L$ can assume the desired value.

For example, to provide a voltage of $V_{C1}$ to L, Q1 and Q4 may be turned on and Q2 and Q3 turned off. The coil L may be connected thusly for an interval of time equal to the pulse widths of voltage pulses received from gate drives $GD_1$ and $GD_2$, which causes the coil current to increase during a first time interval. When the switches are turned off, the coil current commutates to diodes D2 and D3 to capacitor C2 charging C2 and thereby recovering energy in C2. During this phase, the coil current decreases until it is zero at a rate determined by $V_{C2}$. A negative pulse can be generated in a similar fashion by turning on (then off) switches Q2 and Q3 to create a negative current in L (applying a voltage $-V_{C2}$ across coil L) and then switching off to obtain energy recovery in capacitor C1 via diodes D1 and D4. The magnetic field pulses induce approximately rectangular electric field pulses in an organ of a body, which in turn, induce approximately rectangular, adjustable pulse current pulses in an organ body. The exact shape of the magnetic field and electric field pulses is piecewise sinusoidal, resulting from the resonant ringing behavior between the coil L and capacitors C1 and C2. The values of L, C1, and C2 can be chosen so that the piecewise sinusoidal electric field pulse waveform is approximately rectangular in shape.

For other examples, turning on switch Q1 alone may cause a voltage of $V_{C1}$-$V_{C2}$ to be applied across coil L (assuming $V_{C1}$ is higher—If $V_{C2}$ is higher Q3 may be closed). In these cases, one of D1 or D2, respectively, turns on and connects the other terminal of the coil L to C2 or C1, respectively.

Since the switches Q1-Q4 can turn off while the coil current is not zero, snubber circuits $SN_1$-$SN_8$ can be implemented in the circuit to facilitate the turn off of the switches and to reduce the switching losses by taking over part of the switch current during the turn off of the corresponding switch, as well as to suppress ringing in the circuit during switching resulting from parasitic inductances and capacitances in the circuit. Snubber circuits $SN_1$-$SN_8$ can take the form of any of the previously described snubber circuits, as appropriate.

In the circuit embodiment of FIG. 22, the maximum voltage difference between any two parts of the circuit is the higher of $V_{C1}$ and $V_{C2}$. The circuit design may provide the advantage that the maximum voltage required to be withstood by the semiconductor switches Q1 and Q2 as well as D1 and D2 is only $V_{C1}$, and thus, their voltage rating need be no higher than $V_{C1}$ plus a margin for derating and to accommodate transient voltage spikes. Similarly the maximum voltage required to be withstood by the semiconductor switches Q3 and Q4 as well as D3 and D4 is only $V_{C2}$, and thus, their voltage rating need be no higher than $V_{C2}$ plus a margin for derating and to accommodate transient voltage spikes. Switches with lower voltage ratings are generally less costly, smaller, and have lower conduction and switching losses.

Additionally, at the end of the magnetic field pulse, both terminals Vx1 and Vx2 can be connected together by turning Q2 and Q4 on, which then prevents ringing of current in the coil L that would otherwise occur due to the snubber capacitance.

In an embodiment, a 16 µH stimulating coil L, a Powerex CM800HB-66H or CM1200HC-66HH single IGBT module for switch (Q1/D1), a Powerex CM800HB-66H or CM1200HC-66HH single IGBT module for switch (Q2/D2), a Powerex CM800HA-28H or CM1000HA-28H single IGBT module or (½) CM800DZ-34H or (½) CM1000DU-34NF dual IGBT module for switch (Q3/D3), and a Powerex CM800HA-28H or CM1000HA-28H single IGBT module or (½) CM800DZ-34H or (½) CM1000DU-34NF dual IGBT module for switch (Q4/D4) is used to induce approximately rectangular current pulses in the targeted body organ. The energy storage capacitors C1 and C2 have capacitances in the range of 370-740 µF and 1,500-3,000 µF, respectively. These capacitance values can be accomplished with single pulse capacitors or with banks of parallel and/or series connected pulse capacitors with polypropylene dielectrics or paper/oil dielectrics. The maximum setting of voltage $V_{C1}$ is 2,800V and the maximum setting of voltage $V_{C2}$ is 1,000 V. Snubber circuit $SN_1$-$SN_4$ can each include a 0.25 µF capacitor in parallel with series combination of 0.5 µF capacitor and a 1Ω resistor. Snubber circuits $SN_5$-$SN_8$ can be omitted in this embodiment.

The cTMS system disclosed herein enables an operator to adjust various pulse shape parameters (previously described in detail) of an electric field pulse induced in the brain of a patient. The values of these pulse shape parameters can be chosen based on which medical application is being implemented and/or a patient's physiological characteristics. Further, the capability to control pulse parameters enables a medical professional to study the contribution of pulse characteristics to observed physiological effects of an induced electric field pulse.

Additionally, the cTMS systems disclosed herein (see FIGS. 2 and 3) produce approximately rectangular induced electric field pulses, which are more energy efficient for neuronal stimulation than sinusoidal pulses produced by existing TMS systems, as previously described. Moreover, the cTMS systems depicted in FIGS. 2 and 3 also enable an operator to vary the degree of bidirectionality of the induced pulse over a continuous range from a predominantly unipolar to a bipolar electric field pulse.

In view of the effects of the TMS pulse characteristics on physiological responses and the capability of cTMS systems disclosed herein to control the pulse parameters, the cTMS systems disclosed herein have the potential for enabling diverse clinical and research applications. For example, the cTMS systems can be used to determine strength-duration curves (i.e., the induced electric field pulse amplitude vs. the pulse width that produces threshold neuronal stimulation). Strength-duration curves can be used to estimate a neuronal membrane time constant, and can therefore be a useful tool for diagnosing and studying neurological disease. Strength-duration curves can also be used to optimize stimulation paradigms for different cortical regions, and activate selectively different neuronal types possessing different membrane time constants and responsivity to pulse shape characteristics. Thus, the capability to adjust the pulse shape in the cTMS system could enable optimization of the stimulus parameters for various applications.

TMS with briefer, high-amplitude pulses requires less energy delivered to the stimulating coil, thereby increasing efficiency and decreasing heating. Thus, TMS and rTMS with brief (e.g., 20-50 µs) rectangular pulses are more energy efficient.

Recent studies indicate that rTMS with predominately unipolar induced electric fields can yield more potent modulation of neuronal excitability compared to standard bidirectional rTMS.

See for example: M. Sommer, N. Lang, F. Tergau, and W. Paulus, "Neuronal tissue polarization induced by repetitive transcranial magnetic stimulation" Neuroreport, vol. 13, no. 6, pp. 809-11, 2002; A. Antal, T. Z. Kincses, M. A. Nitsche, 0. Bartfai, I. Demmer, M. Sommer, and W. Paulus, "Pulse configuration-dependent effects of repetitive transcranial magnetic stimulation on visual perception," Neuroreport, vol. 13, no. 17, pp. 2229-33, 2002; T. Tings, N. Lang, F. Tergau, W. Paulus, and M. Sommer, "Orientation-specific fast rTMS maximizes corticospinal inhibition and facilitation," Exp Brain Res, vol. 164 no. 3, pp. 323-33, 2005; N. Arai, S. Okabe, T. Furubayashi, Y. Terao, K. Yuasa, and Y. Ugawa, "Comparison between short train, monophasic and biphasic repetitive transcranial magnetic stimulation (rTMS) of the human motor cortex," Clin Neurophysiol, vol. 116, no. 3, pp. 605-13, 2005; and J. L. Taylor and C. K. Loo, "Stimulus waveform influences the efficacy of repetitive transcranial magnetic stimulation," J Affect Disord, vol. 97, pp. 271-276, 2007.

The cTMS system circuit (see FIGS. 2 and 3) is intrinsically energy efficient since the coil transfers charge between two energy-storage capacitors, rather than dissipating it in a resistor, like the conventional monophasic TMS topology does. Further, the cTMS system (see FIGS. 2 and 3) can induce predominately unipolar electric fields with biphasic magnetic pulses having fast rise time and slow fall times, which require substantially less energy delivered to the coil. Thus, such cTMS enables high-frequency unidirectional rTMS, yielding potentially stronger neuromodulation effects that can be used for therapeutic purposes in neurological and psychiatric illness.

Variations, modifications, and other implementations of what is described herein may occur to those of ordinary skill in the art without departing from the spirit and scope of the disclosed subject matter. Further, the various features of the embodiments described herein also can be combined, rearranged, or separated without departing from the spirit and scope of the disclosed subject matter as defined by the following claims.

The invention claimed is:

1. A magnetic stimulation system for inducing approximately rectangular electric field pulses in a body organ, comprising:
    a charging device charging a first electrical energy storage device to an independently selectable first positive voltage (Vc1) and a second electrical energy storage device to an independently selectable second positive voltage (Vc2) whose magnitude is independent of the first positive voltage;
    an operator-controlled device configured to independently select said first and second positive voltages Vc1 and Vc2;
    a stimulating coil;
    a first and a second switching device electrically coupling said first electrical energy storage device to the stimulating coil to produce current pulses with a positive rate of change in the stimulating coil; and
    a third and a fourth switching device electrically coupling said second electrical energy storage device to said stimulating coil to produce current pulses with a negative rate of change in the stimulating coil,
    wherein the stimulating coil is configured to produce, in response to a combination of the current pulses with the positive and negative rates of change, magnetic field pulses that induce predominantly unipolar and approximately rectangular, 20-50 microsecond duration electric filed pulses in the body organ.

2. The system of claim 1, wherein the first electrical energy storage device includes a first capacitor and second electrical energy storage device includes a second capacitor, and the first switching device includes a first semiconductor switch, the second switching device includes a second semiconductor switch, the third switching device includes a third semiconductor switch and the fourth switching device includes fourth semiconductor switch, wherein said first capacitor is electrically coupled to a first terminal of said coil via said first and second semiconductor switches to deliver said first positive voltage Vc1 to said first terminal, and said second capacitor is electrically coupled to a second terminal of said coil via said third and fourth semiconductor switches to deliver said second positive voltage Vc2 to said second terminal.

3. The system of claim 2, further comprising a first and a second diode coupled anti-parallel with the first and the second semiconductor switches, respectively, and a third and a fourth diode coupled anti-parallel with the third and the fourth semiconductor switches, respectively.

4. The system of claim 2, wherein the first, second, third, and fourth semiconductor switches are adapted to switch between an ON and an OFF state, the ON state electrically coupling the first, second, third, and fourth semiconductor switches to the stimulating coil and the OFF state electrically uncoupling the first, second, third, and fourth semiconductor switches from the stimulating coil, so that a voltage across said coil is generated having any one of values 0, Vc1, −Vc2, and Vc1−Vc2, wherein a maximum voltage difference in the system is the larger of the first positive voltage Vc1 and the second positive voltage Vc2.

5. The system of claim 4, wherein a Vc1 voltage across the coil is generated when the first and fourth semiconductor switches are in an ON state and the second and third semiconductor switches are in an OFF state, a −Vc2 voltage across the coil is generated when the second and third semiconductor switches are in an ON state and the first and second semiconductor switches are in an OFF state, and a Vc1−Vc2 voltage across the coil is generated when the first semiconductor switch is in an ON state and the second, third, and fourth semiconductor switches are in an OFF state.

6. The system of claim 5, wherein when the second positive voltage Vc2 is greater than the first positive voltage Vc1, the first semiconductor switch is switched to an OFF state and the third semiconductor switch is switched to an ON state to generate a positive voltage across the coil having a value Vc1−Vc2.

7. The system of claim 1, wherein the operator-controlled device is further configured to selectively adjust over a continuous range of values a plurality of parameters of the induced electric field pulses in the body organ and is further configured to independently control the parameters of the field pulses induced in the body organ, wherein the parameters include pulse amplitude, pulse width, and pulse repetition frequency.

8. The system of claim 7, wherein the first, second, third, and fourth switching devices are adapted to switch between an ON state and an OFF state in response to timing pulses generated by the operator-controlled device, wherein the operator-controlled device is configured to selectively adjust the width of the electrical field pulses induced in the body organ by independently adjusting a time interval in which the first, second, third, and fourth switching devices are in an ON state, wherein adjusting the width of the electrical field pulses induced in the body organ further includes adjusting a first and second phase of the induced electric field pulses independently of each other, the first and second phases having opposite polarity.

9. The system of claim 7, further comprising a detecting device to detect physiological effects induced in the body organ by the electric field pulses, wherein the operator-controlled device is configured to adjust and control the parameters based on the detected physiological effects in the body organ, wherein the physiological effect detected is a voltage change on the neuronal membrane of the body organ.

10. The system of claim 1, wherein the operator-controlled device is further configured to recover some of the energy generated by said current pulses in the stimulating coil and to transfer the recovered energy in one of said electrical energy storage devices to another of said electrical energy storage devices through said charging device.

11. The system of claim 10, wherein the charging device is configured to transfer additional energy to the other electrical energy storage device to supplement the recovered energy to generate a second current in the stimulating coil.

12. The system of claim 11, further comprising generating a train of current pulses, in part, by transferring energy between the first and second electrical energy storage devices such that energy stored in the stimulating coil is repeatedly recovered.

* * * * *